US009624555B2

(12) United States Patent
Hellyer et al.

(10) Patent No.: US 9,624,555 B2
(45) Date of Patent: Apr. 18, 2017

(54) SEQUENCES AND METHODS FOR DETECTING INFLUENZA A AND INFLUENZA B VIRUS

(71) Applicant: Becton, Dickinson and Company, Franklin Lakes, NJ (US)

(72) Inventors: Tobin Hellyer, Westminster, MD (US); James A. Price, Jr., Lutherville, MD (US); Erika L. Jones, Windsor Mill, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 160 days.

(21) Appl. No.: 13/917,456

(22) Filed: Jun. 13, 2013

(65) Prior Publication Data

US 2014/0004502 A1 Jan. 2, 2014

Related U.S. Application Data

(63) Continuation of application No. 12/602,239, filed as application No. PCT/US2008/065289 on May 30, 2008, now abandoned.

(60) Provisional application No. 60/941,270, filed on May 31, 2007.

(51) Int. Cl.
*C12Q 1/70* (2006.01)

(52) U.S. Cl.
CPC .................................... *C12Q 1/701* (2013.01)

(58) Field of Classification Search
None
See application file for complete search history.

(56) References Cited

U.S. PATENT DOCUMENTS

| | | | | |
|---|---|---|---|---|
| 5,985,569 | A * | 11/1999 | Foxall et al. ................ | 435/6.12 |
| 6,682,889 | B1 | 1/2004 | Wang et al. | |
| 2002/0164596 | A1* | 11/2002 | Weimer ............................ | 435/6 |
| 2005/0202414 | A1 | 9/2005 | Jia et al. | |
| 2009/0081648 | A1* | 3/2009 | Wangh .............................. | 435/6 |
| 2009/0098527 | A1 | 4/2009 | Fischer et al. | |
| 2010/0330548 | A1 | 12/2010 | Detmer et al. | |

FOREIGN PATENT DOCUMENTS

| | | | |
|---|---|---|---|
| WO | 9421797 | A1 | 9/1994 |
| WO | 9741257 | A1 | 11/1997 |
| WO | 2004057021 | A2 | 7/2004 |
| WO | 2006110688 | A2 | 10/2006 |
| WO | 2006121773 | A2 | 11/2006 |
| WO | 2007047778 | A2 | 4/2007 |
| WO | 2007058629 | A2 | 5/2007 |
| WO | 2007133682 | A2 | 11/2007 |

OTHER PUBLICATIONS

Li et al. Journal of Clinical Microbiology (2001) 39(2): 696-704.*
Australian Examination Report for Application No. 2008260023 dated Jul. 8, 2013.
Batzer et al. Nucleic Acids Research (1991) 19(18): 5081.
Bustin, S.A. and Nolan, T., 2004, "Basic RT-PCR Considerations," A-Z of Quantitative peR, at pp. 359-395.
Cha, R.S. and Thilly, W.G., 1995, "Specificity, Efficiency, and Fidelity of PCR," PCR Primer: A Laboratory Manual., at pp. 37-62.
Chi X.S. et al.: Journal of Clinical Microbiology 43(5); 2345-2349 (2005), XP008124797.
Communication from EP Application No. 08756512.3, dated Oct. 26, 2011.
Database Genbank [Online] Mar. 26, 2003 'Influenza B virus (B/Saga/S172/99) M, BM2 genes for M1 matrix protein, BM2 protein, complete cds', XP008116476 Database accession No. (AB036877).
Database Genbank [Online] Nov. 26, 2003 'Influenza A virus (A/Yokohama/47/2002(H1N2)) M1, M2 gene for matrix protein 1, matrix protein 2, complete cds', XP008116475 Database accession No. (AB126637).
Hellyer TJ. & Gillespie SH (ed), "Antibiotic Resistance methods and Protocols," Humana, Totowa, NJ, pp. 141-155,2000).
Hellyer, T.I. et ai., Journal of Clinical Microbiology, 37: 518-523, 1999.
Higgins et a1., CARIOS, 5(2):151-153, 1989.
International Search Report, PCT/US2008/065289, dated Oct. 30, 2008.
Little et al, Clinical Chemistry, vol. 45, No. 6, Part 1, pp. 777-784, 1999.
Mehrpouyan, M. et al., Molecular and Cellular Probes, 11:337-347, 1997.
Nadeau et al., "Real-time, Sequence-Specific Detection of Nucleic Acids during Strand Displacement Amplification," Analvtical Biochemistrv, 1999, vol. 276, pp. 177-187.
Nycz, C.M. et al.. Analytical Biochemistry, 259:226-234, 1998.
Spargo, C. A. et ai., Molecular and Cellular Probes, 10:247-256, 1996.
Supplementary European Search Report, EP 08756512, dated Dec. 3, 2010.
Tyagi et al., Molecular Beacons: Probes that Fluoresce upon Hybridization. Nature Biotechnology, 1996, 14: 303-308.
Walker et al.. "Strand Displacement Amplification—An Isothermal, In Vitro DNA Amplification Technique," Nucleic Acids Research. 1992, vol. 20, No. 7. pp. 1691-1696.
Wang, Sha-Sha et al., Clinical Chemistry. 49:1599-1607, 2003.
Whiley D.M. et al.: Diagnostic Microbiology and Infectious Disease, 53; 335-337 (2005), XP005212901.

* cited by examiner

*Primary Examiner* — Angela M Bertagna
(74) *Attorney, Agent, or Firm* — Lerner, David, Littenberg, Krumholz & Mentlik, LLP

(57) ABSTRACT

Nucleic acid amplification primers and methods for specific detection of influenza A and influenza B nucleic acid targets are disclosed. The primer-target binding sequences are useful for detection of influenza A and influenza B targets in a variety of amplification and hybridization reactions. The oligonucleotide sequences are able to differentiate between influenza A and influenza B strains through specific hybridization to one or the other virus strain, enabling specific detection of the presence of influenza A and/or influenza B in a specimen.

14 Claims, 7 Drawing Sheets

Influenza A Virus

Segment 1 (polymerase Pb2)
Segment 2 (polymerase Pb1)
Segment 3 (polymerase PA)
Segment 4 (hemagglutinin; HA)
Segment 5 (nucleoprotein; NP)
Segment 6 (neuraminidase; NA)
Segment 7 (matrix; M1 & M2)
Segment 8 (nonstructural; NS1 & NS2)

Influenza B Virus

Segment 1 (polymerase Pb2)
Segment 2 (polymerase Pb1)
Segment 3 (polymerase PA)
Segment 4 (hemagglutinin; HA)
Segment 5 (nucleoprotein; NP)
Segment 6 (neuraminidase; NA & NB)
Segment 7 (matrix; M1 & M2)
Segment 8 (nonstructural; NS1 & NS2)

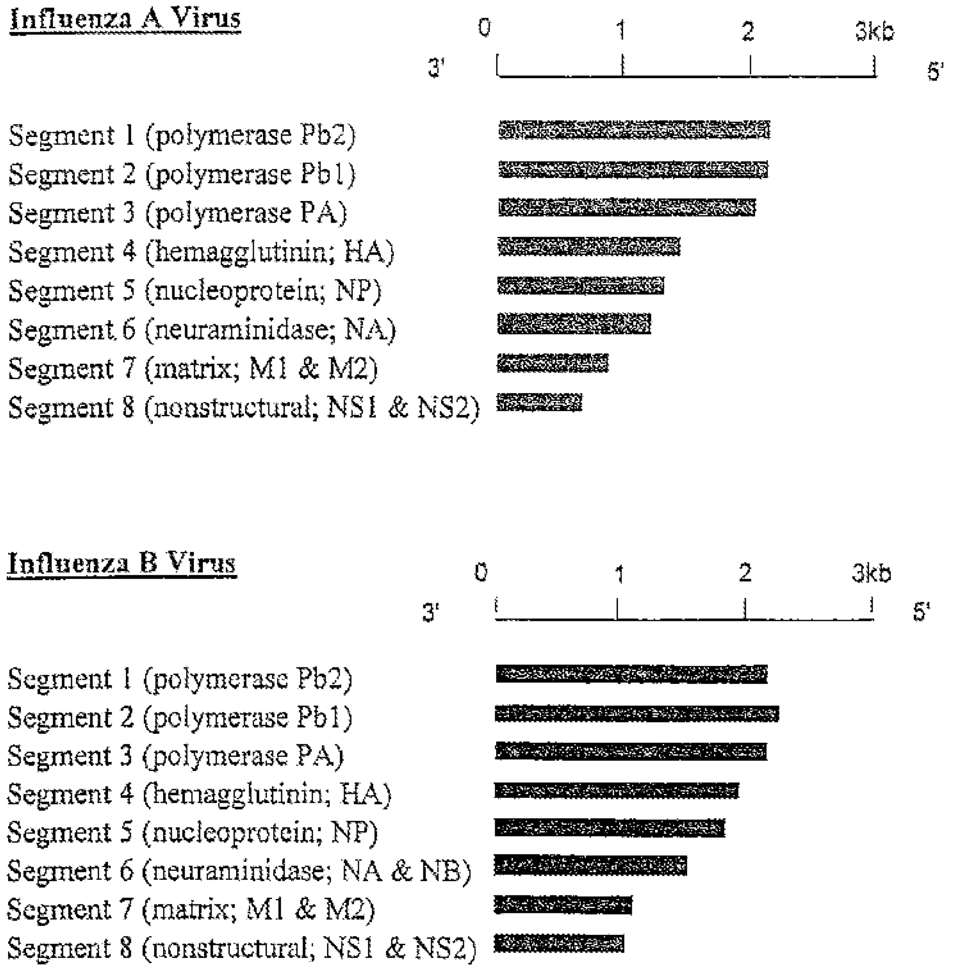

FBM-FB → FBM-FP → ← FBM-Ad

5′-ATGTCGCTGTTTGGAGACACAATTGCCTACCTGCTTTCATTGACAGAAGATGGAGAAGGCAAAGCAGAACTAGCAGAAAA

← FBM-RP

ATTACACTGTTGGTTCGGTGGGAAAGAATTTGACCTAGACTCTGCCTTGGAATGGATAAAAAACAAAAGATGCTTAACTG

← FBM-RB

ATATACAAAAAGCACTAATTGGTGCCTCTATATGCTTTTTAAAACCCAAAGACCAGGAAAGGAAAAGAAGATTCATCACA

GAGCCTCTATCAGGAATGGGAACAACAGCAACAAAAAAGAAAGGCCTGATTCTAGCTGAGAGAAAAATGAGAAGATGTGT

GAGCTTTCATGAAGCATTTGAAATAGCAGAAGGCCATGAAAGCTCAGCGCTACTGTATTGTCTCATGGTCATGTACCTGA

ATCCTGGAAATTATTCAATGCAAGTAAAACTAGGAACGCTCTGTGCTTTGTGCGAGAAACAAGCATCACATTCACACAGG

GCTCATAGCAGAGCAGCGAGATCTTCAGTGCCCGGAGTGAGACGAGAAATGCAGATGGTCTCAGCTATGAACACAGCAAA

AACAATGAATGGAATGGGAAAAGGAGAAGACGTCCAAAAGCTGGCAGAAGAGCTGCAAAGCAACATTGGAGTGTTGAGAT

CTCTCGGAGCAAGTCAAAAGAATGGGGAAGGAATTGCAAAGGATGTAATGGAAGTGCTAAAGCAGAGCTCTATGGGAAAT

TCAGCTCTTGTGAAGAAATATCTATAATGCTCGAACCATTTCAGATTCTTTCAATTTGTTCTTTTATCTTATCAGCTCTC

CACTTCATGGCTTGGACAATAGGGCATTTGAATCAAATAAAAAGAGGAGTAAACATGAAAATACGAATAAAAGGTCCAAA

CAAAGAGACAA -3′

SEQUENCE LISTING

```
<160> NUMBER OF SEQ ID NOS: 77

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: BsoBI
      restriction enzyme recognition site

<400> SEQUENCE: 1

ctcggg                                                                 6


<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Modified
      BsoB1 site with phosphorothioate linkages
<220> FEATURE:
<221> NAME/KEY: misc_feature
<222> LOCATION: (4)..(6)
<223> OTHER INFORMATION: n = a, t, c, or g

<400> SEQUENCE: 2

gagnnn                                                                 6


<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Influenza A
      5' bumper primer

<400> SEQUENCE: 3

tcaggccccc tcaaagc                                                    17


<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Influenza A
      3' bumper primer

<400> SEQUENCE: 4
```

-continued

```
ggcacggtga gcgtgaa                                                17


<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Influenza B
      5' bumper primer

<400> SEQUENCE: 5

tgtcgctgtt tggagac                                                17


<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Influenza B
      3' bumper primer

<400> SEQUENCE: 6

aggcaccaat tagtgctt                                               18


<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Influenza A
      5' amplification primer

<400> SEQUENCE: 7

cgattccgct ccagacttct cgggaggctc tcatggaat                        39


<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Influenza A
      3' amplification primer

<400> SEQUENCE: 8

accgcatcga atgactgtct cgggccctta gtcagaggt                        39


<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Influenza B
      5' amplification primer

<400> SEQUENCE: 9

accgcatcga atgactgtct cgggctttcc caccgaacc                        39


<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Influenza B
      3' amplification primer

<400> SEQUENCE: 10

cgattccgct ccagacttct cgggattgcc tacctgcttt                       40
```

```
<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Influenza A
      adapter primer for universal detection of influenza A RNA

<400> SEQUENCE: 11

acgttagcca ccatacttga gacaggattg gtcttgtctt t                        41


<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Influenza B
      signal primer for universal detection of influenza B RNA

<400> SEQUENCE: 12

acgttagcca ccatacttga gttctgcttt gccttctcca tc                       42


<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Influenza A
      signal primer for detection of internal control RNA

<400> SEQUENCE: 13

actgatccgc actaacgact gacaggattg gtctatctac a                        41


<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Influenza B
      signal primer for detection of internal control RNA

<400> SEQUENCE: 14

actgatccgc actaacgact agttctgctt tgccttccac ct                       42


<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Target
      Reporter Probe

<400> SEQUENCE: 15

tccccgagta cgttagccac catacttga                                      29


<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Internal
      Control Reporter Probe

<400> SEQUENCE: 16

tccccgagta ctgatccgca ctaacgact                                      29
```

-continued

```
<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Influenza A
      5' Amplification primer #2

<400> SEQUENCE: 17

cgattccgct ccagacttct cgggaggctc tcatggagt                              39


<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Influenza A
      5' Amplification primer #2

<400> SEQUENCE: 18

cgattccgct ccagacttct cgggtgaggc tctcatgga                              39


<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Influenza A
      5' target sequence

<400> SEQUENCE: 19

aggctctcat ggaat                                                        15


<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Influenza A
      3' target sequence

<400> SEQUENCE: 20

cccttagtca gaggt                                                        15


<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Influenza B
      5' target sequence

<400> SEQUENCE: 21

ctttcccacc gaacc                                                        15


<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Influenza B
      3' target sequence

<400> SEQUENCE: 22

attgcctacc tgcttt                                                       16
```

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Influenza A 5' target sequence

<400> SEQUENCE: 23
aggctctcat ggagt 15

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Influenza A 5' target sequence

<400> SEQUENCE: 24
tgaggctctc atgga 15

<210> SEQ ID NO 25
<211> LENGTH: 719
<212> TYPE: DNA
<213> ORGANISM: Artificial Sequence
<220> FEATURE:
<223> OTHER INFORMATION: Description of Artificial Sequence: Fig. 3 - influenza A matrix gene

<400> SEQUENCE: 25
atgagccttc taaccgaggt cgaaacgtgt gttctctcta tcgttccatc aggccccctc 60
aaagccgaaa tcgcgcagag acttgaagat gtctttgctg ggaaaaacac agatcttgag 120
gctctcatgg aatggctaaa gacaagacca attctgtcac ctctgactaa ggggattttg 180
gggtttgtgt tcacgctcac cgtgcccagt gagcgaggac tgcagcgtag acgctttgtc 240
caaaatgccc tcaatgggaa tggggatcca aataacatgg acaaagcagt taaactgtat 300
agaaaactta agagggagat aacattccat ggggccaaag aaatagcact cagttattct 360
gctggtgcac ttgctagttg catgggcctc atatacaata ggatgggggc tgtaaccacc 420
gaagtggcat ttggcctggt atgtgcaaca tgtgaacaga ttgctgactc ccagcacagg 480
tctcataggc aaatggtggc aacaaccaat ccattaataa aacatgagaa cagaatggtt 540
ttggccagca ctacagctaa agctatggag caaatggctg gatcaagtga gcaggcagcg 600
gaggccatgg agattgctag tcaggccagg caaatggtgc aggcaatgag aaccgttggg 660
actcatccta gttccagtac tggtctaaga gatgatcttc ttgaaaattt gcagacctta 719

<210> SEQ ID NO 26
<211> LENGTH: 891
<212> TYPE: DNA
<213> ORGANISM: Artificial Sequence
<220> FEATURE:
<223> OTHER INFORMATION: Description of Artificial Sequence: Fig. 4 - influenza B matrix gene

<400> SEQUENCE: 26
atgtcgctgt ttggagacac aattgcctac ctgctttcat tgacagaaga tggagaaggc 60
aaagcagaac tagcagaaaa attacactgt tggttcggtg ggaaagaatt tgacctagac 120
tctgccttgg aatggataaa aaacaaaaga tgcttaactg atatacaaaa agcactaatt 180
ggtgcctcta tatgcttttt aaaacccaaa gaccaggaaa ggaaaagaag attcatcaca 240

-continued

```
gagcctctat caggaatggg aacaacagca acaaaaaaga aaggcctgat tctagctgag    300

agaaaaatga gaagatgtgt gagctttcat gaagcatttg aaatagcaga aggccatgaa    360

agctcagcgc tactgtattg tctcatggtc atgtacctga atcctggaaa ttattcaatg    420

caagtaaaac taggaacgct ctgtgctttg tgcgagaaac aagcatcaca ttcacacagg    480

gctcatagca gagcagcgag atcttcagtg cccggagtga gacgagaaat gcagatggtc    540

tcagctatga acacagcaaa aacaatgaat ggaatgggaa aaggagaaga cgtccaaaag    600

ctggcagaag agctgcaaag caacattgga gtgttgagat ctctcggagc aagtcaaaag    660

aatggggaag gaattgcaaa ggatgtaatg gaagtgctaa agcagagctc tatgggaaat    720

tcagctcttg tgaagaaata tctataatgc tcgaaccatt tcagattctt tcaatttgtt    780

cttttatctt atcagctctc cacttcatgg cttggacaat agggcatttg aatcaaataa    840

aaagaggagt aaacatgaaa atacgaataa aaggtccaaa caaagagaca a             891
```

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 27
tcaggccccc tcaaag 16

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 28
tcgggccccc tcaaag 16

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 29
tcgggccccc tcaaaa 16

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 30
tcaggccccc tcaaaa 16

<210> SEQ ID NO 31
<211> LENGTH: 18
<212> TYPE: DNA
<213> ORGANISM: Artificial Sequence -continued

```
<220> FEATURE:
<223> OTHER INFORMATION: Description of Artificial Sequence: Synthetic
      PCR oligonucleotide primer

<400> SEQUENCE: 31

gaggctctca tggaatgg                                                 18


<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 32

gaagctctca tggaatgg                                                 18


<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 33

gaagttctca tggaatgg                                                 18


<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 34

gaagcactca tggaatgg                                                 18


<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 35

gaagctctca tggagtgg                                                 18


<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 36

gaagtactca tggaatgg                                                 18


<210> SEQ ID NO 37
<211> LENGTH: 18
<212> TYPE: DNA
<213> ORGANISM: Artificial Sequence
<220> FEATURE:
```

-continued

<223> OTHER INFORMATION: Description of Artificial Sequence: Synthetic
      PCR oligonucleotide primer

<400> SEQUENCE: 37
gaagtactca tggagtgg 18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 38
gaagcactca tggagtgg 18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 39
gaagttctca tggagtgg 18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 40
gaggttctca tggaatgg 18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 41
gaggtactca tggaatgg 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 42
gaggttctca tggagtgg 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic -continued PCR oligonucleotide primer

<400> SEQUENCE: 43
gaggtactca tggagtgg 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 44
gaggcactca tggaatgg 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 45
gaggcactca tggagtgg 18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 46
gaggctctca tggagtgg 18

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 47
aaagacaaga ccaatcctgt cacctc 26

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 48
aaagacaaga ccgatcctgt cacctc 26

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide probe -continued

<400> SEQUENCE: 49
aaagacaaga ccgattctgt cacctc 26

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
PCR oligonucleotide probe

<400> SEQUENCE: 50
aaagacaaga ccgatcttgt cacctc 26

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
PCR oligonucleotide probe

<400> SEQUENCE: 51
aaagacaaga ccgatcctgt cacctt 26

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
PCR oligonucleotide probe

<400> SEQUENCE: 52
aaagacaaga ccgattttgt cacctc 26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
PCR oligonucleotide probe

<400> SEQUENCE: 53
aaagacaaga ccgattttgt cacctt 26

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
PCR oligonucleotide probe

<400> SEQUENCE: 54
aaagacaaga ccgattctgt cacctt 26

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
PCR oligonucleotide probe

<400> SEQUENCE: 55
aaagacaaga ccgatcttgt cacctt 26

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 56
aaagacaaga ccaattctgt cacctc 26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 57
aaagacaaga ccaattttgt cacctc 26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 58
aaagacaaga ccaattttgt cacctt 26

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 59
aaagacaaga ccaattctgt cacctt 26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 60
aaagacaaga ccaatcttgt cacctc 26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 61

-continued aaagacaaga ccaatcttgt cacctt 26

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 62
aaagacaaga ccaatcctgt cacctt 26

<210> SEQ ID NO 63
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 63
tgggcacggt gagcgt 16

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 64
tgggcacggt gagtgt 16

<210> SEQ ID NO 65
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 65
gcacggtgag cgtgaa 16

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 66
gcacggtgag tgtgaa 16

<210> SEQ ID NO 67
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 67
gcacggtgag tgtaaa 16

<210> SEQ ID NO 68
<211> LENGTH: 16
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 68
gcacggtgag cgtaaa 16

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic PCR oligonucleotide primer

<400> SEQUENCE: 69
tgtcgctgtt tggagacac 19

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 70
atggagaagg caaagcagaa ctag 24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 71
atggagaagg caaagcagag ctag 24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 72
atggagaagg caaagcagag ttag 24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic PCR oligonucleotide probe

<400> SEQUENCE: 73
atggagaagg caaagcagaa ttag 24

-continued

```
<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 74

ttctttccca ccgaacca                                                  18


<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 75

ctctttccca ccgaacca                                                  18


<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 76

ctctttccca ccaaacca                                                  18


<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR oligonucleotide primer

<400> SEQUENCE: 77

ttctttccca ccaaacca                                                  18
```

SEQUENCES AND METHODS FOR DETECTING INFLUENZA A AND INFLUENZA B VIRUS

CROSS-REFERENCE TO RELATED APPLICATIONS

The present application is a continuation, of U.S. patent application Ser. No. 12/602,239, filed on Nov. 30, 2009, which application is a national phase entry under 35 U.S.C. §371 of International Application No. PCT/US 2008/065289 filed May 30, 2008, which claims priority from 60/941,270 filed May 31, 2007, all of which are hereby incorporated herein by reference.

SEQUENCE LISTING

The instant application contains a Sequence Listing which has been submitted in ASCII format via EFS-Web and is hereby incorporated by reference in its entirety. Said ASCII copy is named BECTON136_sequencelisting.txt and is 21818 bytes in size.

FIELD OF THE INVENTION

The present invention relates to nucleic acid primers and probes derived from influenza A and influenza B viruses and methods for specific detection of influenza using nucleic acids that hybridize specifically to either influenza A or influenza B nucleic acids. The oligonucleotides and methods disclosed are useful for detection of influenza A and influenza B targets in a variety of amplification and hybridization reactions. The oligonucleotide sequences are able to differentiate between influenza A and influenza B strains through specific hybridization to influenza A or influenza B nucleic acids, enabling specific detection of the presence of influenza A and/or influenza B in a specimen.

BACKGROUND

There are three known influenza genera: genus A, genus B and genus C. Influenza belongs to the family of viruses referred to as myxoviruses, and more specifically to orthomyxoviruses. This family also includes "Thogoto-like" viruses. The orthomyxoviruses infect vertebrates. Virions in this family have a genome containing 7 to 8 segments of linear, negative-sense, single stranded RNA. (See, FIG. 2). Genomes of the influenza viruses are from 12000 to 15000 nucleotides in length.

Influenza types A and B are distinguishable based on the surface antigens hemagglutinin (H), which binds to host cells, and neuraminidase (N), which cleaves budding viruses from infected cells. Influenza A may be further classified into subtypes H1 to H16 and N1 to N9 based on the virus-encoded hemagglutinin and neuraminidase proteins, respectively. The influenza B virus is not further classified into subtypes. The influenza virus genome mutates continuously, resulting in frequent appearance of new antigenic variants and causing seasonal epidemics.

The oligonucleotides and methods disclosed are useful for detection of influenza A and influenza B nucleic acid targets in a variety of amplification and hybridization reactions. The present invention provides a more rapid and sensitive means of specifically detecting influenza A and B compared to previously known techniques (immunological and culture-based methods). Furthermore, the nucleic acids of the present invention are useful in various nucleotide amplification techniques, as described in further detail herein.

DESCRIPTION OF THE FIGURES

FIG. 2. Schematic representation of the Influenza A (A/Ong Kong/1073/99, H9N2) and B (B/Memphis/12/97) virus RNA genomes. Based on GenBank Accession Nos. NC-004906-NC004912 and NC-004783-NC004790, respectively. (The information can be accessed at the following website: www.uq.edu.au/vdu/VDUInfluenza).

FIG. 4. SEQ ID NO:26, which is a partial nucleotide sequence map of influenza B matrix gene showing location of primers corresponding to the regions of complementarity to influenza RNA sequences (not including additional 5' and 3' non-influenza sequences). FBM-FB=5' bumper primer, FBM-FP=5' amplification primer, FBM-AD=signal primer for universal detection of influenza RNA, FBM-RP=3' amplification primer, FBM-RB=3' bumper primer. The Reporter Probe MPC D/R that hybridizes to the complement of the 5' tail of the signal primer (the adapter sequence) is not shown.

DETAILED DESCRIPTION OF THE INVENTION

Figure 1A:
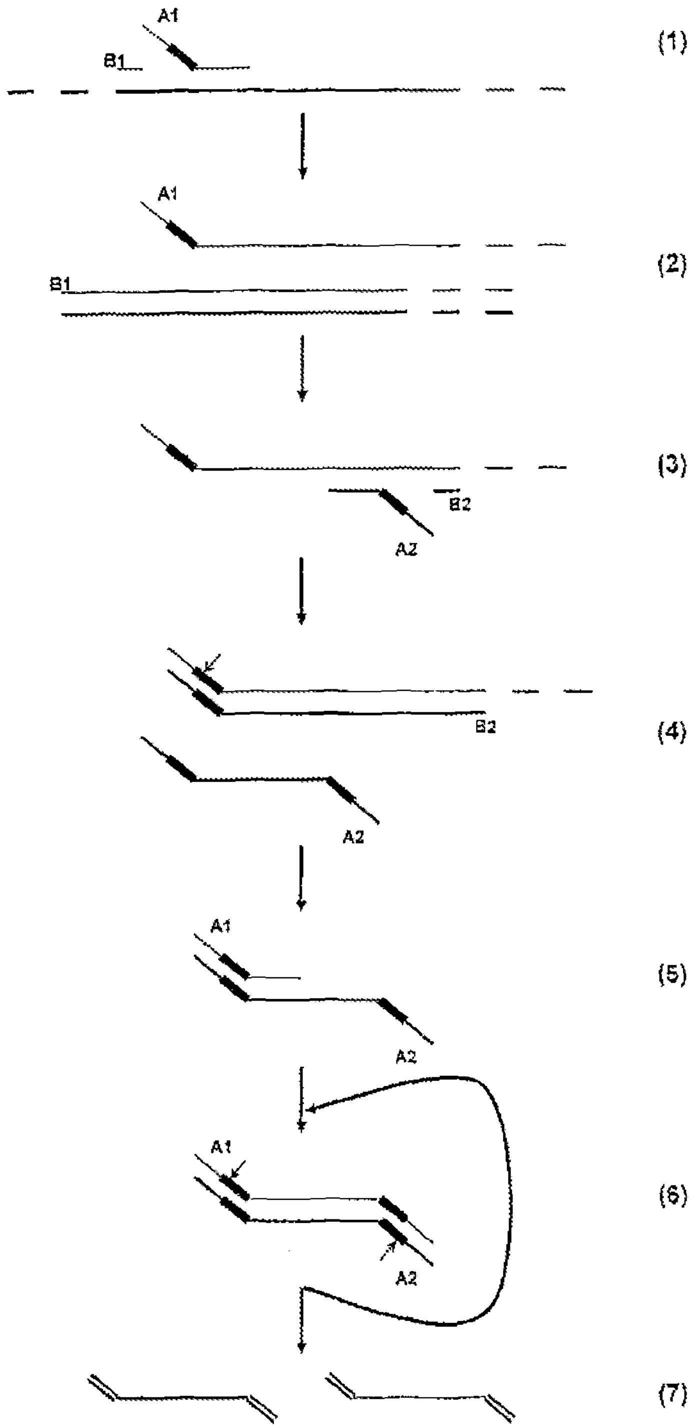
FIG. 1. Schematic representation of Strand Displacement DNA Amplification (SDA). A. B1 and B2 symbolize "bumper" primers. A1 and A2 symbolize "amplification" primers. Primers A1 and A2 may contain a restriction enzyme recognition site, for instance, the nucleotide sequence 5'-C-T-C-G-G-G-3' (SEQ ID NO:1), which corresponds to the BsoBI restriction enzyme recognition site. The complementary nucleotide sequence generated during SDA in the presence of phosphorothioate-modified nucleotides contains the complementary sequence to the restriction enzyme recognition site. If this site is BsoBI, the complementary sequence generated is 5'-Cs-Cs-Cs-G-A-G-3' (SEQ ID NO:2), wherein "s" preferably symbolizes a phosphorothioate linkage. Restriction enzyme BsoB1 cleaves nucleotides between the first and second nucleotide at the 5' end of the recognition sequence but cannot cleave between nucleotides joined by a phosphorothioate bond. (1) Bumper primer B1 hybridizes to single-stranded DNA target sequence upstream of S1. (2) DNA polymerase extension from the 3' ends of B1 and A1 results in the displacement of the A1 extension product into solution. (3) A2 and upstream B2 hybridize to the displaced A1 extension product. (4) Extension from the 3' end of B2 displaces the downstream A2 extension product. (5) Hybridization of an A1 primer to the displaced A2 extension product. (6) Extension from the 3' end of hybridized A1 results in the formation of a double-stranded molecule with nickable restriction sites at either end. (7) Nicking of the unmodified DNA strands by the restriction enzyme and polymerase extension from the restriction sites displaces single-stranded molecules into solution that possess partial restriction enzyme recognition sites at either end. These single-stranded molecules then feed into the exponential phase of SDA depicted in FIG. 1B, while the double-stranded parent molecule is regenerated and becomes available for subsequent rounds of nicking, extension and displacement. B. Exponential Amplification. (1) Displaced single-stranded molecules generated by the sequence of events depicted in FIG. 1A hybridize to amplification primers A1 and A2. (2) The 3' ends of the amplification primer and the displaced strand are extended by DNA polymerase, creating double-stranded target fragments, each of which is flanked by a hemi-modified restriction enzyme recognition site that is in turn nicked by the restriction enzyme. Polymerase extends from the 3' end at the site of the nick, regenerating the double-stranded fragment (including the nickable restriction site) and simultaneously displacing the downstream DNA strand into solution. (3) Displaced single-stranded molecules with partial restriction enzyme recognition sites at either end circulate back into step (1) to bring about exponential amplification. C. SDA with universal detection. (1-3) A signal primer, S1, comprising a target-specific 3' sequence, T, and a 5' generic (or "universal") tail (the adapter sequence), G, that hybridizes to the amplified target downstream of an amplification primer, A1. DNA polymerase extension from the 3' ends of both the signal primer and upstream amplification primer results in displacement of the signal primer extension product into solution, which in turn, hybridizes to a complementary amplification primer, A2. (4) Extension from the 3' ends of the amplification primer and signal primer extension product generates the complement of the 5' adapter tail sequence and a double-stranded restriction recognition site. (5) Nicking of the restriction site and extension from the nick displaces a single-stranded copy of the signal primer complement into solution. (6) The displaced sequence hybridizes to a complementary fluorescent reporter probe that possesses the generic sequence G at its 3' end. (7) Extension from the 3' ends of the reporter probe and its target sequence results in generation of a double stranded restriction recognition sequence. (8) Maximum fluorescence is obtained by complete separation of the quencher and fluorophore via cleavage of the double-stranded reporter probe restriction site. D. Direct detection with a target-specific reporter probe. (1) Reporter probe R hybridizes downstream of A1. (2) DNA polymerase extends from the 3' ends of S1 and R. Extension of S1 displaces the downstream extension product of R into solution where it hybridizes to a complementary amplification primer, A2. (3) Extension from the 3' end of A2 results in formation of a double stranded restriction site. (4-5) Fluorescent signal is generated by cleavage of the restriction site and complete separation of the fluorophore and quencher.

The present invention provides nucleotide primers and probes derived from influenza A and influenza B virus genomes and methods for specific detection of influenza A and influenza B through hybridization and/or nucleotide amplification. The primer-target binding sequences are useful in methods for specifically amplifying and/or hybridizing to influenza A and influenza B genome sequence targets in a variety of amplification and detection reactions or direct hybridization assays. The primer-target binding sequences allow specific detection of influenza A and/or influenza B target nucleic acids and enable determination of the presence of either influenza A or influenza B, or both, in a specimen containing one or both of influenzas A and B and/or other unrelated viruses and/or microscopic organisms. Kits comprising the primers and probes of the present invention are also disclosed and are useful in performing the methods of the present invention.

The present invention may be described by, but not necessarily limited to, the following exemplary embodiments. Any one embodiment of the invention might not exhibit all of the advantages provided by the invention, and different embodiments may provide different advantages. While the invention is described in certain embodiments herein, this invention can be further modified within the spirit and scope of this disclosure. This invention is therefore intended to encompass any variations, uses, or adaptations of the invention using the invention's general principles. Further, this invention includes such variations on the present disclosure as come within known or customary practice in the art to which this invention pertains and which fall within the limits of the appended claims.

The present invention discloses novel oligonucleotides useful as primers and probes and methods of specifically detecting influenza A and B in a sample containing either one or both strains of influenza and/or other unrelated viruses/microscopic organisms. The present invention further discloses kits comprising the novel oligonucleotides of the present invention useful in performing the methods of the present invention. The nucleotide sequences of the primers and probes of the present invention are designed to hybridize specifically to regions of the influenza A and influenza B genomes that are unique to the genome of each strain, but which are also conserved across many viruses within each strain. Thus, one embodiment of the present invention is oligonucleotide probes and primers which specifically hybridize to these taxonomically unique regions of the influenza A and influenza B genome and which are therefore useful in detecting the presence of influenza A and/or influenza B in a sample. Thus, the oligonucleotides of the present invention do not cross-hybridize under assay conditions as described herein to nucleic acids from other influenza virus types. Furthermore, the oligonucleotides of the present invention do not cross-hybridize under assay conditions as described herein to nucleic acids from viruses that are not related to influenza.

The oligonucleotides of the present invention may be used in various nucleic acid amplification techniques known in the art, such as, for example, Polymerase Chain Reaction (PCR), Nucleic Acid Sequence Based Amplification (NASBA), Transcription-Mediated Amplification (TMA), Rolling Circle Amplification (RCA), Strand Displacement Amplification (SDA), thermophilic SDA (tSDA) or Ligation-Mediated Amplification (LMA). A further example of tSDA is homogeneous fluorescent real time tSDA. The oligonucleotides of the present invention may also be used in a variety of methods known to one of ordinary skill in the art for direct detection of influenza A and B without amplification through direct hybridization with viral nucleic acids, or to detect DNA or RNA copies of viral nucleic acids, or their complements.

In a further embodiment, the oligonucleotides of the present invention may be utilized in any of the various amplification and/or hybridization detection reactions to determine whether only influenza A is present in a sample. Also, kits are disclosed which provide for the specific detection of only influenza A through amplification and/or hybridization techniques.

In a further embodiment, the oligonucleotides of the present invention may be utilized in any of the various amplification and/or detection reactions mentioned to determine whether only influenza B is present in a sample. Also, kits are disclosed which provide for the specific detection of only influenza B through amplification and/or hybridization techniques.

The specimen from which nucleic acid material is tested may be any biological specimen, such as, but not limited to, nasopharyngeal, nasal and throat swabs as well as nasopharyngeal aspirates and washes. The specimen may undergo preliminary processing prior to testing (several preliminary processing protocols are known) to allow more efficient detection of the viral nucleic acid. For example, the sample may be collected and may be added to transport medium to stabilize the virus. Nasopharyngeal, nasal and throat swabs are preferably added to a transport medium. Nasopharyngeal aspirates and washes may or may not be stabilized by addition of transport medium. Once received at the testing laboratory, the virus may be inactivated and lysed to liberate the viral RNA. The nucleic acid may optionally then be extracted to remove potential inhibitors or other interfering agents of later assay steps. To perform the methods of the invention, viral nucleic acids may be mixed with components essential for specific detection of influenza A and/or influenza B.

The oligonucleotides of the present invention also include oligonucleotides comprising detectable moieties. For instance, detectable moieties useful in the present invention may include, but are not limited to, donor-quencher dye pairs such as fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), FITC/rhodamine X, FITC/tetramethylrhodamine (TAMRA), and others. P-(dimethyl aminophenylazo)benzoic acid (DABCYL) is a non-fluorescent quencher dye that effectively quenches fluorescence from an adjacent fluorophore such as fluorescein, 5-(2'-aminoethyl)aminonaphthalene or rhodamine. Other preferred oligonucleotide labels include, but are not limited to, single fluorophores such as fluorescein and rhodamine, radioactive labels such as $^{32}P$ and $^{35}S$, enzymes such as horseradish peroxidase, alkaline phosphatase, glucose oxidase, β-galactosidase, soybean peroxidase or luciferase and haptens such as digoxigenin, biotin and 2,4-dinitrophenyl.

Oligonucleotides of the present invention include SEQ ID NOS:3-24 and 27-77 and oligonucleotides that specifically hybridize to nucleic acids having sequences that are the complement of SEQ ID NOS: 3-24 and 27-77 under assay conditions. Assay conditions include, for example, those used for tSDA reactions conducted at 52.5° C.: 143 mM bicine, 82 mM KOH, 24.5 mM $KPO_4$, 12.5% DMSO, 1.67% glycerol, 100 ng/μl BSA, 2 ng/μl yeast RNA, 100 nM each of dATP, dGTP, dTTP, 500 nM dCsTP, and 6.7 mM magnesium acetate.

Figure 3:
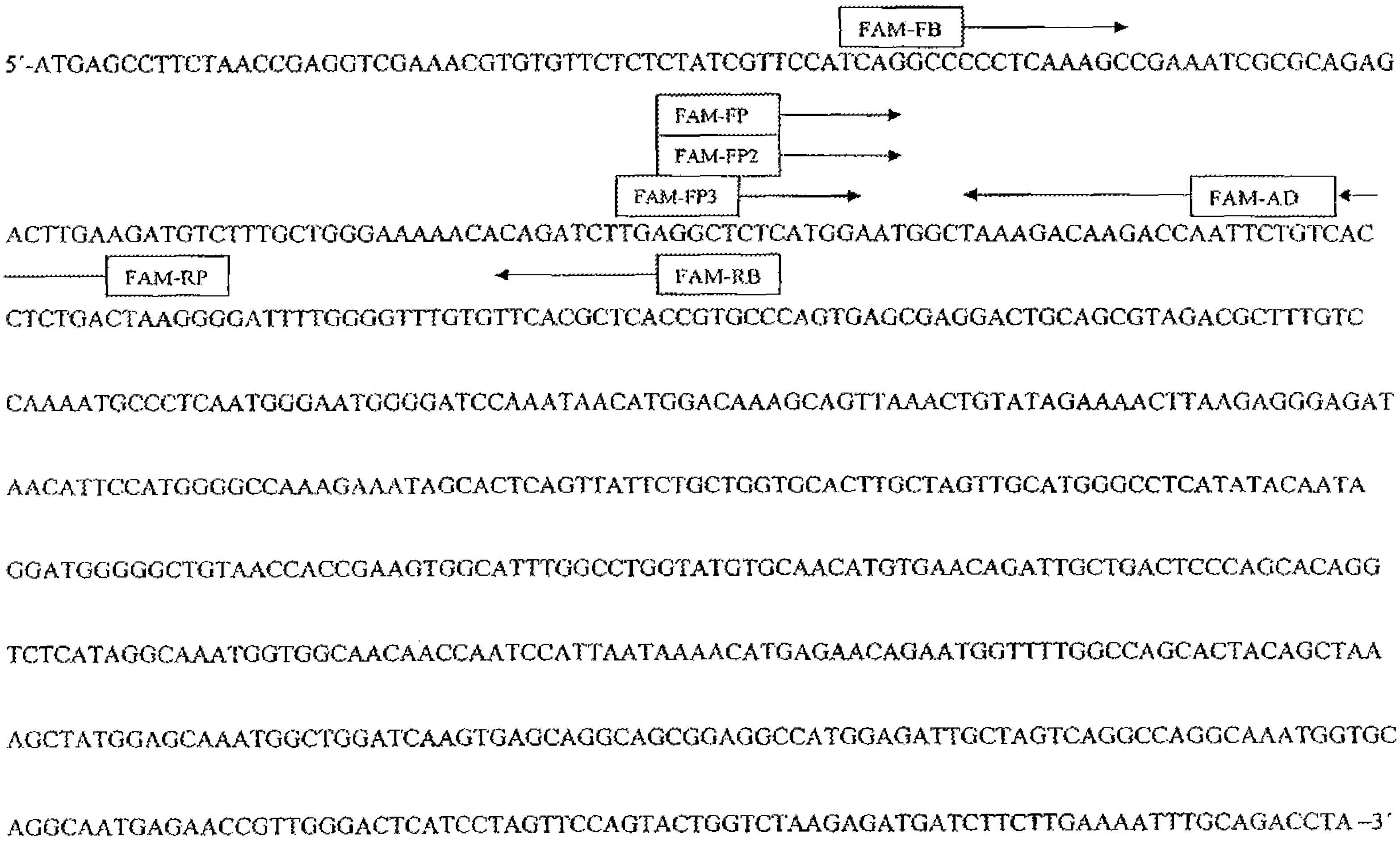
FIG. 3. SEQ ID NO:25, which is a partial nucleotide sequence map of a representative influenza A matrix gene showing the location of primers corresponding to the regions of complementarity to the influenza A RNA sequences (not including additional 5' and 3' non-influenza sequences). FAM-FB=5' bumper primer, FAM-FP=5' amplification primer, FAM-AD=signal primer for universal detection of Influenza A, FAM-RP=3' amplification primer, FAM-RB=3' bumper primer. The Reporter Probe MPC D/R that hybridizes to the complement of the 5' tail of the signal primer (the adapter sequence) is not shown.

The oligonucleotides of the present invention include target-binding sequences such as SEQ ID NOS: 19-24 and 27-77. These sequences correspond to influenza A and B matrix gene sequences which are highly conserved within either A- or B-type influenza. For instance, SEQ ID NOS: 19, 20, 23 and 24 are highly conserved within the Influenza A type. The nucleotide sequence of SEQ ID NO:19 corresponds to nucleotides 119-133 of an influenza A matrix gene as provided in SEQ ID NO:25, and as depicted in FIG. 3. Further, the target-binding sequence of SEQ ID NO:20 is the same as SEQ ID NO:19 except that one nucleotide is changed. Thus, primers consisting essentially of these sequences will hybridize to a sequence complementary to the same region of SEQ ID NO:25. Furthermore, SEQ ID NO:23 corresponds to nucleotide positions 117-131 of SEQ ID NO:25 and SEQ ID NO:24 corresponds to nucleotide positions 159-173 of SEQ ID NO:25. It is expected that these target-binding regions within the influenza A matrix gene may be adjusted by as many as 12 nucleotides in either the 5' or 3' direction, or both, within SEQ ID NO:25, or a region corresponding to this sequence within any influenza A matrix gene, and the same results of the present invention may be achieved. Regarding influenza B target-binding sequences SEQ ID NOS: 21 and 22, corresponding to nucleotide positions 22-37 and 92-106 of SEQ ID NO:26, it is expected that oligonucleotides of the present invention designed to hybridize specifically to these regions may be adjusted by up to 12 nucleotides in length or position in either the 5' or 3' direction, or both, within SEQ ID NO:26, or a region corresponding to this sequence within any corresponding influenza B matrix gene, and the same specificity for hybridizing to influenza B type may be achieved.

Furthermore, oligonucleotides of the present invention comprising these target-binding sequences, such as, for instance, SEQ ID NO:9, corresponding to the 3' amplification primer, as listed in Table 1, below, which has an underlined portion corresponding to the target-binding sequence CTTTCCCACCGAACC (SEQ ID NO:21), may likewise have a sequence corresponding to this target-binding sequence which is altered by extending or shifting this underlined portion in either the 5' or 3' direction, or both, to encompass up to 12 additional nucleotides in either direction. This would apply to any oligonucleotide comprising the target-binding sequence of the present invention, such as the oligonucleotides corresponding to SEQ ID NOS: 7-10.

Oligonucleotides of the present invention also include bumper primers that may be used in methods according to the present invention. A bumper primer consisting essentially of the sequence according to SEQ ID NO:3 is exemplary of a 5' bumper primer that could be used in a detection method to specifically detect the presence of influenza A, and corresponds to nucleotides 49-65 of the influenza A matrix gene (SEQ ID NO:25). Other bumper primers disclosed herein as examples include SEQ ID NO:4, corresponding to nucleotides 190-206 of the influenza A matrix gene (SEQ ID NO:25), SEQ ID NO:5, corresponding to nucleotides 2-18 of the influenza B matrix gene (SEQ ID NO:26), and SEQ ID NO:6, corresponding to nucleotides 170-187 of the influenza B matrix gene (SEQ ID NO:26). As with the target-binding sequences and amplification primers discussed above, it is expected that each one of these bumper primers may be adjusted in either the 5' or 3' direction, or both, by about 12 nucleotides, or more, and still function to achieve the desired method results, i.e. to specifically detect the presence of either influenza A or influenza B, or both.

That is, it is expected that the oligonucleotides of the present invention, designed to specifically hybridize to either influenza A or influenza B matrix gene sequences, according to, for instance, SEQ ID NOS:19, 20, 23 and 24 for the influenza A type, and 21 and 22 for influenza B type, may be adjusted in position and length and still achieve specific hybridization to influenza A or influenza B matrix genes. Oligonucleotides of the present invention encompass these variations as one of ordinary skill in the art knows that specificity may be achieved using such altered oligonucleotides.

Hybridization and/or amplification using the oligonucleotides of the present invention can be achieved over a broad range of chemistry and thermal conditions using thermophilic SDA, mesophilic SDA and PCR conditions. Several examples in which thermophilic SDA has been employed to hybridize and amplify DNA or RNA target sequences have been reported. (See, Spargo, C. A. et al., *Molecular and Cellular Probes,* 10:247-256, 1996; Nadeau, J. G. et al., *Analytical Biochemistry,* 276:177-187, 1999; Nycz, C. M. et al., *Analytical Biochemistry,* 259:226-234, 1998; and Hellyer, T. J. et al., *Journal of Clinical Microbiology,* 37: 518-523, 1999).

Examples describing reaction conditions for hybridization and/or amplification using mesophilic SDA have also been reported. Mesophilic SDA requires modification of the 5' (non-hybridization region) sequence within the amplification primers and reporter probes and use of alternative restriction enzymes such as, for example, Ava I, that perform optimally at lower temperatures relative to thermophilic SDA, as well as use of a polymerase enzyme with a temperature optimum in the desired range (e.g., exo$^-$-Klenow polymerase for temperatures between approximately 35-42° C.). Use of alternative restriction enzymes may also require incorporation of an alternative modified nucleotide such as, for example, mesophilic SDA with the Hindi restriction enzyme requires use of thioated-dATP in place of the dCsTP used with thermophilic BsoBI-based assay systems. (See, Walker, G. T. et al., *Nucleic Acids Research,* 20:1691-1696, 1992; Mehrpouyan, M. et al., *Molecular and Cellular Probes,* 11:337-347, 1997; Little, M. C. et al., *Clinical Chemistry,* 45:777-784, 1999; and Wang, Sha-Sha et al., *Clinical Chemistry,* 49:1599-1607, 2003).

The oligonucleotides of the present invention can also be used in a broad range of PCR conditions to hybridize and/or amplify target sequences. Such conditions have been reported previously concerning the design of PCR conditions and troubleshooting techniques that can be used to optimize hybridization and/or amplification of target sequences. (See, Cha, R. S. and Thilly, W. G., 1995, "Specificity, Efficiency, and Fidelity of PCR," *PCR Primer: A Laboratory Manual.*, at pp. 37-62, Cold Spring Harbor Laboratory Press, Plainview, N.Y.; Roux, K., Id. at pp. 37-62; Bustin, S. A. and Nolan, T., 2004, "Basic RT-PCR Considerations," *A-Z of Quantitative PCR*, at pp. 359-395, International University Line, La Jolla, Calif.; and Altshuler, M. L., 2006, *PCR Troubleshooting: The Essential Guide*, Caister Academic Press, Norfolk, UK).

One of ordinary skill in the art knows that nucleic acids do not require complete complementarity in order to hybridize. Thus, the probe and primer sequences disclosed herein may be modified without loss of utility as influenza matrix gene-specific probes and primers. One of ordinary skill in the art also knows that hybridization of complementary and nucleic acid sequences that are not 100% complementary may be obtained by adjustment of the hybridization conditions to increase or decrease stringency. Absent indications to the contrary, such minor modifications of the disclosed sequences and any necessary adjustments of hybridization conditions to maintain influenza virus specificity are considered variation within the scope of the invention.

Oligonucleotides of one embodiment of the present invention that may be used, for instance, in an SDA reaction, are as shown in Table 1. Regions of complementarity to influenza RNA sequences are underlined, restriction enzyme recognition sites (such as BsoBI) are italicized. Intentional mutations made to the internal control signal primers relative to the influenza signal primers are in bold type, and are designed to hybridize to internal nucleic acids optionally added to an assay, in a manner mimicking amplification of target sequence and using the same amplification and bumper primers.

TABLE 1

| SEQ ID NO: | NAME | DESCRIPTION & SEQUENCE |
|---|---|---|
| 3 | FAM-FB | Influenza A 5' bumper primer<br>TCAGGCCCCCTCAAAGC |
| 4 | FAM-RB | Influenza A 3' bumper primer<br>GGCACGGTGAGCGTGAA |
| 5 | FBM-FB | Influenza B 5' bumper primer<br>TGTCGCTGTTTGGAGAC |
| 6 | FBM-RB | Influenza B 3' bumper primer<br>AGGCACCAATTAGTGCTT |
| 7 | FAM-FP | Influenza A 5' amplification primer<br>CGATTCCGCTCCAGACTT*CTCGGG*AGGCTCTCATGGAAT |
| 8 | FAM-RP | Influenza A 3' amplification primer<br>ACCGCATCGAATGACTGT*CTCGGG*CCCTTAGTCAGAGGT |
| 9 | FBM-RP | Influenza B 3' amplification primer<br>ACCGCATCGAATGACTGT*CTCGGG*CTTTCCCACCGAACC |
| 10 | FBM-FP | Influenza B 5' amplification primer<br>CGATTCCGCTCCAGACTT*CTCGGG*ATTGCCTACCTGCTTT |
| 11 | FAM-AD | Influenza A signal primer for universal detection of influenza A RNA<br>ACGTTAGCCACCATACTTGAGACAGGATTGGTCTTGTCTTT |
| 12 | FBM-AD | Influenza B signal primer for universal detection of influenza B RNA<br>ACGTTAGCCACCATACTTGAGTTCTGCTTTGCCTTCTCCATC |
| 13 | FAMICA.2 | Influenza A signal primer for detection of internal control RNA<br>ACTGATCCGCACTAACGACTGACAGGATTGGTCT**ATCTACA** |
| 14 | FBMICA.2 | Influenza B signal primer for detection of internal control RNA<br>ACTGATCCGCACTAACGACTAGTTCTGCTTTGCCTT**CCACCT** |

TABLE 1-continued

| SEQ ID NO: | NAME | DESCRIPTION & SEQUENCE |
|---|---|---|
| 17 | FAM-FP2 | Influenza A 5'amplification primer<br>CGATTCCGCTCCAGACTT*CTCGGG*AGGCTCTCATGGAGT |
| 18 | FAM-FP3 | Influenza A 5'amplification primer<br>CGATTCCGCTCCAGACTT*CTCGGG*TGAGGCTCTCATGGA |

In one embodiment, oligonucleotides of the present invention may consist of a sequence selected from among SEQ ID NOS: 19-24 and additionally may comprise additional nucleotides such as, especially, a restriction enzyme recognition site (RERS). In one embodiment of the present invention, the RERS is a BsoBI site. Other restriction enzyme sites useful in the present invention include, but are not limited to, for example, HincII, AvaI (an isoschizomer of BsoBI), NciI and Fnu4HI.

In another embodiment, oligonucleotides of the invention may consist of, or consist essentially of, one or more polynucleotides having the nucleotide sequence of SEQ ID NOS:3-24 and 27-77. In yet another embodiment, oligonucleotides having the nucleic acid sequences according to SEQ ID NOS: 3-24 may be utilized in an SDA reaction to determine whether influenza A and/or influenza B is present in a sample. (See, for instance, the methods of Nadeau et al. as disclosed in U.S. Pat. Nos. 5,547,861, 6,656,680, 6,743,582 and 6,316,200). SDA is illustrated schematically in FIGS. 1A and 1B. For example, the disclosed primers and probes can be used in SDA in a manner that is analogous to the signal primer reaction described in U.S. Pat. No. 5,547,861.

In essence, a signal primer (S1) having a 3' target binding sequence and a noncomplementary 5' tail hybridizes to the target sequence downstream from an amplification primer (A1). (FIG. 1C, Step (1)). As illustrated in FIG. 1C, the entire hybridization site of the signal primer is downstream from the hybridization site of the amplification primer. However, the hybridization sites of the signal primer and the amplification primer on the target may also partially overlap (typically only by several nucleotides, preferably from about 1 to about 12 nucleotides) without significantly affecting the methods of the invention. As used herein, the term "downstream from," with respect to the hybridization sites of the signal primer and the amplification primer on the target, generally encompasses nonoverlapping and partially overlapping sequences in the target.

In one embodiment there is a pair of amplification primers a) and b) or c) and d). Primer a) has any one of SEQ ID NOS: 7, 8, 19, 23 or 24, and, optionally, an additional sequence, and primer b) has any one SEQ ID NO: 17, 18 or 20, and, optionally, an additional sequence. Primer c) has a target binding sequence selected from SEQ ID NO: 9 or 21, and, optionally, an additional sequence, and primer d) has a target binding sequence selected from SEQ ID NO: 10 or 22, and, optionally, an additional sequence. In one specific embodiment primers a) and b) consist essentially of SEQ ID NOS: 7 or 8 and SEQ ID NOS: 17 or 18, respectively. Primers c) and d) consist essentially of SEQ ID NOS: 9 and 10, respectively. As noted above, the additional sequences in the pair of amplification primers can be a restriction endonuclease recognition site that is nickable by a restriction endonuclease. Examples of restriction endonuclease recognition sites include: BsoBI, HincII, AvaI, NciI and Fnu4HI.

In Step (2), of FIG. 1C, the amplification primer and the signal primer are simultaneously extended by polymerase reaction. Extension of the amplification primer displaces the single-stranded signal primer extension product (FIG. 1C, Step (2)). In the third step, the second amplification primer (A2) hybridizes to the signal primer extension product (FIG. 1C, Step (3)). Step (4) provides for extension of the amplification primer and signal primer extension product to produce a double-stranded secondary amplification product with a hemimodified RERS at one end (FIG. 1C, Step (4)). Nicking of the unmodified S2 strand of the RERS, extension from the nick and displacement of the downstream strand produces a single-stranded oligonucleotide that comprises the complement of the signal primer (FIG. 1C, Step (5)) and which in turn hybridizes to the 3' tail of the reporter probe (FIG. 1C, Step (6)). Extension from the 3' ends of the reporter probe and signal primer complement results in formation of a double-stranded restriction site (FIG. 1C, Step (7)). Fluorescent signal is generated through the double-stranded cleavage of the restriction site and separation of the fluorophore and quencher moieties (FIG. 1C, Step (8)). The complement of the signal primer and the double-stranded secondary amplification product are produced only when the target is present and amplified. These oligonucleotides can therefore be detected as an indication of target amplification.

According to the detection method depicted in FIG. 1C, the double-stranded secondary amplification product may be detected. However, this is only meant to be illustrative of one of several possible embodiments of this one type of detection method. There are many different possible detection methods for which the oligonucleotides of the present invention may be useful.

Figure 1B:
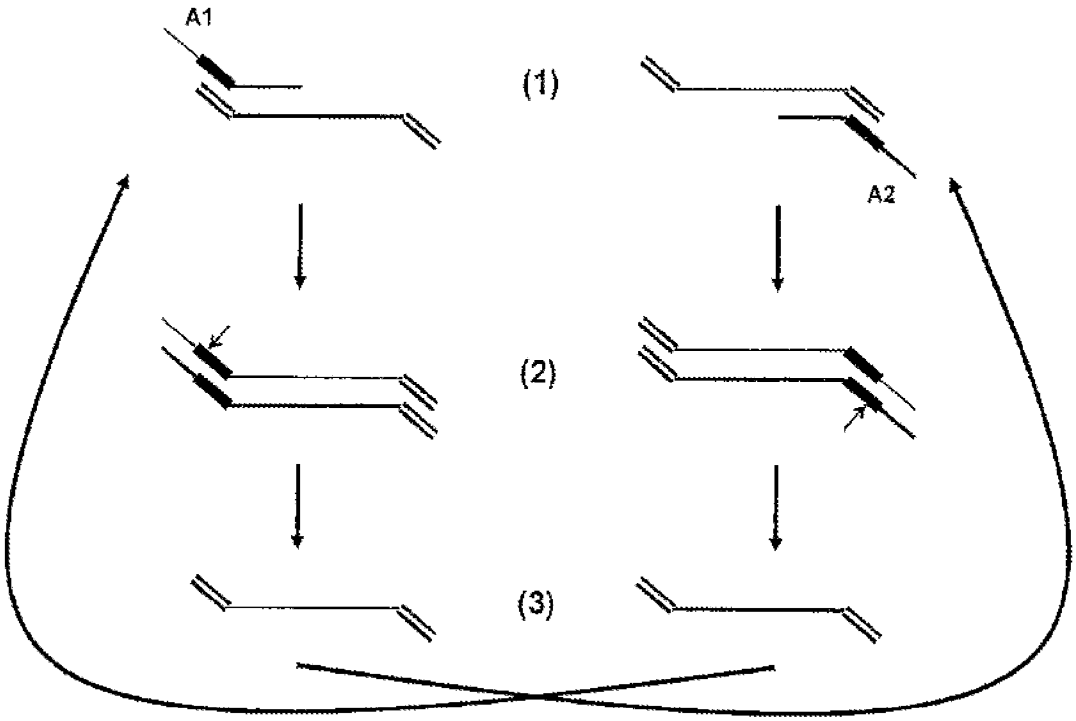
Figure 1C:
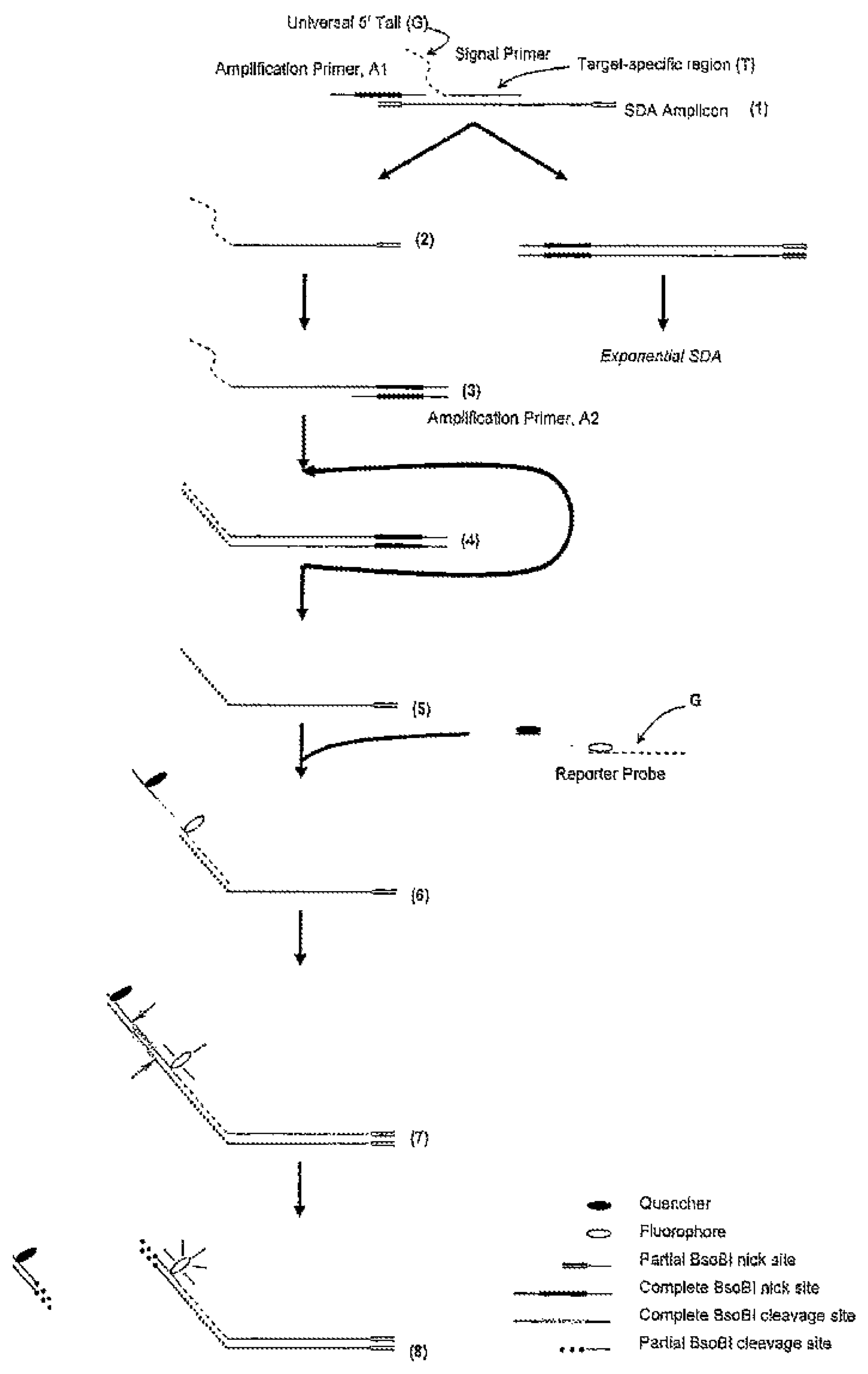
Figure 1D:
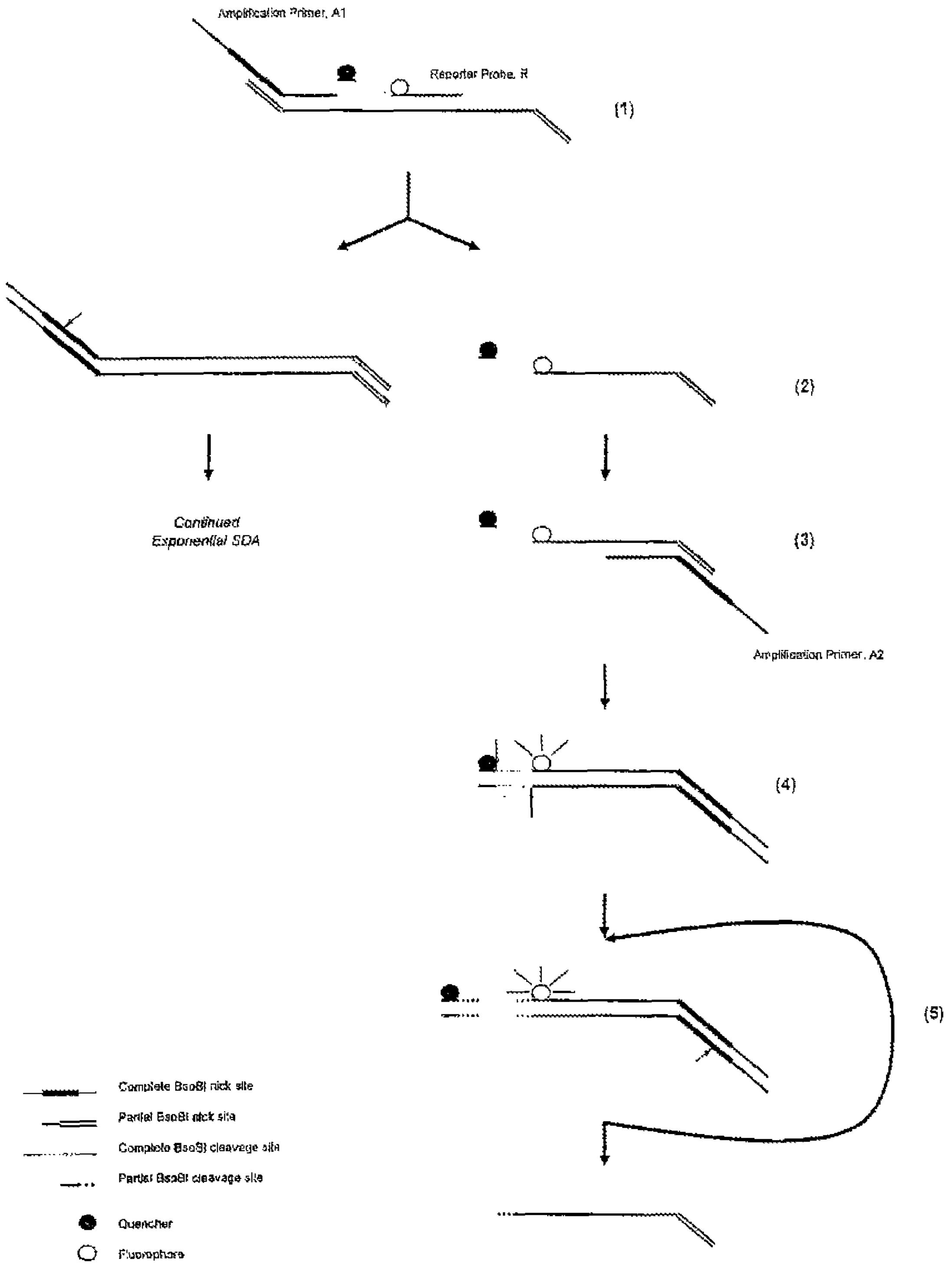

For instance, in another embodiment of the method depicted by FIG. 1B, the single-stranded oligonucleotides of Step (3) may be detected directly by hybridization to a reporter molecule (FIG. 1D).

In a further embodiment of the method depicted in FIG. 1, a hairpin reporter detectable moiety labeled with a donor/quencher pair, which are typically dyes, may be utilized such that donor fluorescence is quenched in the SDA reaction. (See, for instance, U.S. Pat. No. 5,928,869). In one embodiment the detectable moiety is detectable by a change in resonance energy transfer. It will be appreciated by one of ordinary skill in the art that it may not be necessary for the detectable moiety to be rendered entirely double-stranded to be detected. For example, a partial complement of the hairpin structure can be sufficient to keep the arms of the stem of the hairpin from hybridizing to each other.

As used herein, "double-stranded reporter moiety" is intended to encompass both fully and partially double-stranded reporter moieties provided they are sufficiently double-stranded to render the reporter moiety detectable. When the reporter moiety is rendered double-stranded in the primer extension reaction, the hairpin is unfolded. Upon unfolding, the donor and quencher become sufficiently spatially separated to reduce or eliminate quenching of donor fluorescence by the quencher. The resulting increase in donor fluorescence, or a change in another fluorescence parameter associated with a change in fluorescence quenching (such as, for example, fluorescence lifetime, fluorescence polarization or a change in emission of the quencher/acceptor), may be detected as an indication of amplification of the target sequence.

In addition, multiple detectable reporter moieties may be combined in a single reporter probe. For example, a labeled hairpin may comprise a single-stranded RERS in the single-stranded "loop." In this embodiment synthesis of the complement of the reporter moiety not only unfolds the hairpin to produce an increase in fluorescence, the RERS concurrently becomes cleavable or nickable, which may produce an additional fluorescence increase.

In another embodiment, the folded detectable reporter moiety (e.g., a hairpin) of the reporter probe does not hybridize to the complement of an adapter sequence. However, in an alternative embodiment, the adapter sequence may be selected so that its complementary sequence will hybridize to all or part of a folded reporter moiety of the reporter probe. In this embodiment, hybridization alone will unfold or partially unfold the reporter moiety to produce a signal without the need for polymerase-catalyzed extension following hybridization. The folded detectable reporter moiety in this embodiment may comprise all or part of the reporter probe's sequence. In an example of such an embodiment, the reporter probe may be a molecular beacon, a hairpin oligonucleotide in which the loop of the beacon hairpin comprises all or part of the adapter sequence. (See, for example, Tyagi and Kramer, *Nature Biotech.,* 14:303-308, 1996). As the complement of the adapter sequence is synthesized during target amplification, it binds to the molecular beacon and unfolds the structure, producing increased fluorescence.

Thermophilic Strand Displacement Assays, as described in U.S. Pat. Nos. 5,648,211 and 5,744,311, may also be performed using the nucleic acids of the present invention. Because the enzymes employed are thermolabile (i.e., temperature sensitive), conventional mesophilic SDA as described by Walker et al. (*Nucleic Acids Research,* 20:1691-1696, 1998) is conducted at a constant temperature between about 37° C. and 42° C. The enzymes that drive the amplification reaction are inactivated as the reaction temperature is increased. However, the ability to conduct isothermal SDA at higher temperatures using thermostable enzymes, such as the restriction enzyme BsoBI and Bst DNA polymerase, has several advantages. For example, amplification at elevated temperatures allows for more stringent annealing between amplification primers and template DNA, thereby improving the specificity of the amplification process and potentially reducing background reactions. A significant source of background reactions are short "primer dimers" that are generated when the amplification primers interact with one another, impairing the efficiency of the desired amplification of the target sequence through the consumption of rate limiting reagents. The formation of such primer dimers is more likely at lower temperatures because the reduced stringency of the reaction allows increased possibility of transient hybridization between sequences with limited homology. The ability to conduct SDA at higher temperatures reduces the likelihood of primer dimer interactions, suppresses background amplification and improves the efficiency of amplification of specific target. In addition, amplifying at higher temperatures in the range of 50° C. to 70° C. is likely to facilitate strand displacement by the polymerase which, in turn, would increase the efficiency of target amplification and result in increased yields of amplified product.

Thus, in some embodiments of the invention, the oligonucleotides of the present invention will anneal to their intended targets under conditions appropriate for use of thermostable enzymes. It is considered that, at least for specific target-binding sequences, the annealing will be specific to the degree that influenza A-specific oligonucleotides anneal to influenza A nucleic acid and not to influenza B nucleic acid, influenza C nucleic acid, or non-influenza nucleic acids, at a temperature of from about 50° C. to about 70° C. in a solution of from about 50 to about 500 mM alkali metal ion (usually potassium ion), preferably about 100 to 200 mM alkali metal ion, or equivalent solution conditions.

In another embodiment of the method of the present invention, the reporter probe may be designed to comprise a single-stranded sequence 3' to the folded reporter moiety such that both the single-stranded sequence and all or part of the folded reporter moiety hybridize to the sequence complementary to the adapter sequence as it is produced during amplification.

In other alternative embodiments, other reporter moieties may be substituted in the reaction scheme shown in FIG. 1. For example, other folded nucleic acid structures, such as G-quartets, may be substituted and unfolded in a similar target-dependent manner to reduce fluorescence quenching. Alternatively, a specialized linear sequence may be used as the reporter moiety, for example a RERS, as depicted in FIG. 1C. When a RERS is used as the reporter moiety, the donor and quencher are linked flanking a cleavage site so that when the RERS is rendered double-stranded and cleaved in a target-dependent manner the donor and quencher are separated onto separate nucleic acid fragments. These alternative structures may also be combined with specialized sequences, such as an RERS in a G-quartet. The RERS may alternatively be rendered nickable rather than cleavable in its double-stranded form. This is a particularly suitable embodiment for use in SDA, as incorporation of modified nucleotides and production of nickable RERS's are an integral part of the amplification reaction in the SDA method.

As noted above, kit embodiments are also contemplated herein. Kits that include at least one oligonucleotide, where the oligonucleotide has at least a sequence of one of the oligonucleotide sequences from either the group of SEQ ID NOS: 7-10 or the group of 17-24. Specifically the kit contains an oligonucleotide that is either one of SEQ ID NOS: 3, 4, 7, 8, 17 and 18 or one of SEQ ID NOS: 5, 6, 9 and 10. The oligonucleotide further comprises a reporter probe comprising a detectable moiety. In a further embodiment the kit has one or more oligonucleotides that has at least a nucleic acid sequence selected from one of SEQ ID NOS: 7, 8, 17 and 18 or one or more oligonucleotides that has at least the nucleic acid sequence selected from the group consisting of SEQ ID NOS: 3 and 4. In yet another embodiment the kit has one more oligonucleotides consisting essentially of a nucleic acid sequence selected from the group consisting of SEQ ID NO: 11 and 13, but with optional additional sequences such as RERS sequences as described above.

These embodiments are merely variations of a myriad different methods of detection utilizing the oligonucleotides of the present invention and available to one of ordinary skill in the art for the specific detection and/or amplification of influenza genomes. Further variations of standard methods of Polymerase Chain Reaction (PCR), Nucleic Acid Sequence Based Amplification (NASBA), Transcription-Mediated Amplification (TMA), Rolling Circle Amplification (RCA) or Ligation-Mediated Amplification (LMA) may also be utilized as well as other methods of detection by amplification or direct hybrization.

For instance, oligonucleotides consisting of, or consisting essentially of, one or more of the nucleotide sequences of SEQ ID NOS:27-77 may be used as primers in a PCR reaction designed to specifically amplify either influenza A DNA or influenza B DNA or both, in samples containing a mixture of the two viruses or just one of the viruses or no virus (as a control). In addition to these oligonucleotides, oligonucleotides comprising such analogs as xanthine and/or inosine at positions of degeneracy may be employed. Examples of positions of degeneracy include one or more of the following substitutions:

position 3 of SEQ ID NOS:27-30 substituted with inosine or xanthine,
position 16 of SEQ ID NOS:27-30 substituted with inosine or xanthine,
position 3 of SEQ ID NOS:31-46 substituted with inosine or xanthine,
position 5 of SEQ ID NOS:31-46 substituted with inosine,
position 6 of SEQ ID NOS:31-46 substituted with inosine or xanthine,
position 15 of SEQ ID NOS:31-46 substituted with inosine or xanthine,
position 13 of SEQ ID NOS:47-62 substituted with inosine or xanthine,
position 16 of SEQ ID NOS:47-62 substituted with inosine,
position 17 of SEQ ID NOS:47-62 substituted with inosine,
position 26 of SEQ ID NOS:47-62 substituted with inosine,
position 14 of SEQ ID NOS:63 and 64 substituted with inosine,
position 11 of SEQ ID NOS:65-68 substituted with inosine,
position 14 of SEQ ID NOS:65-68 substituted with inosine or xanthine,
position 20 of SEQ ID NOS:70-73 substituted with inosine or xanthine,
position 21 of SEQ ID NOS:70-73 substituted with inosine,
position 1 of SEQ ID NOS:74-77 substituted with inosine and
position 13 of SEQ ID NOS:74-77 substituted with inosine or xanthine.

Such an embodiment allows sensitive and specific detection of these viruses in a sample using standard PCR techniques.

In another embodiment, influenza A and influenza B are detected in a single multiplex reaction. For example, influenza A and B may be detected in the same SDA reaction using amplification and signal primers that are specific for each organism. Reporter probes labeled, for example, with different dyes then enable the detection and distinction of amplified products from the two different species in the same reaction vessel.

In yet another embodiment an internal amplification control is included in the same reaction i.e., in a triplex reaction, such that detection of the internal amplification control can be used to verify the performance of the assay. In the absence of either of the specific analytes (i.e., influenza A and B), detection of the amplification control serves to verify that conditions were appropriate for success of the reaction.

In another embodiment, detection of influenza A and B may be conducted in a reaction mixture which also contains primers and probes for the detection of other viral respiratory and/or non-respiratory analytes such as, for example, coronaviruses (including, for example, Severe Acute Respiratory Syndrome-associated Coronavirus), parainfluenza viruses 1, 2, 3 and 4, respiratory syncytial virus, adenoviruses, rhinoviruses, parvoviruses, rotaviruses, noroviruses, herpes viruses and enteroviruses.

In a further embodiment, detection of influenza A and B is conducted in a reaction mixture which also contains primers and probes for the detection of respiratory and/or non-respiratory bacterial or fungal analytes such as, but not limited to, *Legionella* spp., *Streptococcus* spp., *Mycoplasma* spp., *Chlamydia* spp., *Bordetella* spp, *Pneumococcus* spp., *Cryptococcus* spp., *Candida* spp. and *Pneumocystis* spp.

In another embodiment of the invention, detection of influenza A and B may be conducted using a microarray that is coated with specific capture probes. Different capture probes for different viral, bacterial or fungal analytes are deposited at different locations on the surface of the array. Isolated nucleic acid from the analytes of interest may be hybridized directly to the surface of the microarray or may undergo amplification by methods known in the art, as already disclosed herein, such as PCR, SDA, TMA, NASBA or rolling circle amplification. Hybridization of nucleic acid to the specific capture probes may be detected by a variety of different methods including, but not limited to, the use of fluorescently-labeled reporter probes, chemiluminescence and electrochemistry. In these embodiments, one or more of the oligonucleotides of the present invention may be used as a capture probe or as a detection reagent.

DEFINITIONS

Influenza A and B are enveloped viruses consisting of segmented, negative strand RNA and are the causative agents of highly contagious, acute respiratory disease. Influenza A and B viruses are morphologically indistinguishable. These viruses are classified based on antigenic differences in the nucleoprotein (NP) and matrix (M) protein. Influenza A viruses are further classified into subtypes according to properties of the two major glycoproteins expressed on the surface of the viruses: hemagglutinin and neuraminidase.

An "amplification primer" is a primer for amplification of a target sequence by extension of the primer after hybridization to a target sequence. For SDA, the 3' end of the amplification primer (the target-binding sequence) hybridizes to the intended target at the 3' end of the target-binding sequence. The amplification primer may comprise a recognition site for a restriction endonuclease near its 5' end. The recognition site is for a restriction endonuclease which will cleave one strand of a DNA duplex when the recognition site is hemimodified ("nicking"), as described in, for example, U.S. Pat. No. 5,455,166 and U.S. Pat. No. 5,270,184 and EP 0684315. As no special sequences or structures are required to drive the amplification reaction, amplification primers for PCR may consist only of target binding sequences. Amplification primers for 3SR and NASBA, in contrast, may further comprise an RNA polymerase promoter near the 5' end. The promoter is appended to the target-binding sequence and serves to drive the amplification reaction by directing transcription of multiple RNA copies of the target. Amplification primers are approximately 10-75 nucleotides in length, preferably about 15-50 nucleotides in length. Typically a stretch of contiguous nucleotides of about 10-25 nucleotides in length hybridizes to the target and confers specificity of hybridization to the amplification primer.

A "signal primer" according to the present invention comprises a 3' target binding sequence that hybridizes to a complementary sequence in the target and further comprises a 5' tail sequence that is not complementary to the target (the adapter sequence). The adapter sequence is selected such that its complementary sequence will hybridize to the 3' end of the reporter probe described below. In some embodiments of the present invention, the signal primer does not comprise a detectable label. Signal primers are typically approximately 10-75 nucleotides in length, preferably about 15-50 nucleotides in length. The typical length of a signal primer depends on the method in which it is used. The length of a signal primer for SDA, for instance, is typically about 25-50 nucleotides. The 3' end of a signal primer is the target binding sequence and hybridizes to the target sequence. Typically a stretch of contiguous nucleotides of about 10-25 nucleotides in length hybridizes to the target and confers hybridization specificity on the signal primer. The specificity of a signal primer may be different from the specificity of an amplification primer used in the same assay. For example, amplification primer target binding sequences might be specific to influenza A or B, while signal primer target binding sequences might be specific for influenza A and B.

In SDA-type methods, a signal primer according to the present invention may comprise a 5' tail sequence that is not complementary to the target, called an "adapter sequence." The adapter sequence is selected such that its complementary sequence will hybridize to the 3' end of a reporter probe and may constitute a detectable label. In various embodiments of the present invention, the adapter sequence is selected such that its complementary sequence binds to both the 3' end of the reporter probe and to a sequence within the reporter moiety of a reporter probe. In some embodiments of the invention, the signal primer does not comprise a detectable label.

The "target binding sequence" of a primer is the portion that determines the target-specificity of the primer. That is, the essential function of a target-specific sequence is to specifically bind or hybridize to the target nucleic acid. For amplification methods that do not require specialized sequences at the ends of the target binding sequence, the amplification primer generally consists essentially of only the target binding sequence. For example, amplification of a target sequence using PCR according to the present invention may employ amplification primers consisting essentially of the target binding sequences. In such instances, the amplification primer may be labeled with a directly detectable label, such as a fluorophore or a radioisotope, an enzyme or an immunologic tag such as a hapten or peptide epitope. Some amplification methods require specialized sequences appended to the target binding sequence, such as than the nickable restriction endonuclease recognition site and the tail of a primer appropriate for use in SDA, or e.g., an RNA polymerase promoter for 3SR, NASBA or TAS, the required specialized sequence may be linked to the target binding sequence using routine methods for preparation of oligonucleotides without altering the hybridization specificity of the primer.

As used herein, the terms "primer" and "probe" refer to functions of an oligonucleotide. A primer is typically extended by a polymerase enzyme or by ligation following hybridization to a target sequence. A probe might or might not be extended. A hybridized oligonucleotide may function as a probe if it is used to capture or detect a target sequence, and the same oligonucleotide may function as a primer when it is employed as a target binding sequence of an amplification primer. It will therefore be appreciated that any of the target binding sequences disclosed herein for amplification, detection or quantitation of influenza may also be used either as hybridization probes or as target binding sequences in primers for detection or amplification, optionally linked to a specialized sequence required by the selected amplification reaction or to facilitate detection.

A "bumper primer" is a primer used to displace primer extension products in isothermal amplification reactions, such as SDA. As described in U.S. Pat. No. 5,744,311, the bumper primer anneals to a target sequence upstream of the amplification primer such that extension of the bumper primer displaces the downstream amplification primer and its extension product. In other embodiments of the present invention, extension of bumper primers may also be used to displace the downstream extension products of signal primers as described in U.S. Pat. No. 6,316,200. Bumper primers may optionally be target-specific.

The terms "target" or "target sequence" refer to nucleic acid sequences to be amplified or detected. These include the original nucleic acid sequence to be amplified, its complement and either strand of a copy of the original sequence, which is produced by replication, or amplification. These copies serve as further amplifiable targets because they contain copies of the sequence to which the amplification primers hybridize. Copies of the target sequence which are generated during the amplification reaction are referred to as "amplification products," "amplimers," or "amplicons." In the context of the present invention, the terms target or target sequence refer to specific nucleic acid sequences to which primers or probes hybridize and which exhibit homology or complementarity to a part of the genomes of either influenza A or influenza B, or to a transcript or clone of one (or perhaps both) of these viruses. In addition, a target sequence may also be derived from some other source, in order to serve as either a positive control or as a normalizing control in a quantitative assay. Furthermore, in a multiplex format assay, a plurality of analytes, which may include non-influenza A, non-influenza B analytes, may be present in a sample, and primer and probe sequences may be appropriately derived for such additional targets.

The term "extension product" refers to the copy of a target sequence produced by hybridization of a primer and extension of the primer by a polymerase enzyme using the target sequence and sequences adjacent thereto as a template.

The term "assay probe" refers to any oligonucleotide used to facilitate detection or identification of a nucleic acid sequence. Signal primers as described above, and detector probes, detector primers, capture probes and reporter probes as described below are examples of assay probes.

The terms "amplicon," "amplification product" and "amplimer" refer to the product of the amplification reaction generated through the extension of either or both of a pair of amplification primers. An amplicon may contain exponentially amplified nucleic acids generated by two or more primers that hybridize to a target sequence. Alternatively, amplicons may be generated by linear amplification by hybridization of a single primer to the target sequence. Thus, the term amplicon is used generically herein and does not imply the presence of exponentially amplified nucleic acids.

A "reporter probe" according to the present invention comprises a label which is preferably at least one donor/quencher dye pair, i.e., a fluorescent donor dye and a quencher for the donor fluorophore. The label is linked to a structure in the reporter probe (the "reporter moiety"), which does not hybridize directly to the target sequence. This structure may be a nucleotide sequence.

In one embodiment of the invention, the sequence of the reporter probe 3' to the reporter moiety is selected to hybridize to the complement of the signal primer adapter sequence. In general in this embodiment, the 3' end of the reporter probe does not contain sequences with any significant complementarity to the target sequence. In some instances, however, the reporter probe may contain the sequence that hybridizes to the adapter complement and another short sequence at the 3' end that hybridizes to a short segment of the target complement. In this case, the region of target complementarity is not large enough to permit significant hybridization without concurrent hybridization of the adapter-specific region of the reporter probe. The label of the reporter probe is detected as an indication of the presence of a complement of the reporter moiety that renders it double-stranded, thereby indicating the presence of or the amplification of the target.

Any nucleic acid sequence or structure, which can be labeled such that the presence of its complement, generated according to the methods of the invention, indicates the presence of the target sequence, can serve as the reporter moiety of the reporter probe. Preferably, the reporter moiety is labeled with a donor/quencher dye pair such that donor fluorescence is quenched prior to detection of a target and such that quenching of donor fluorescence is reduced as an indication of the presence of the target. The reporter moiety may be a secondary structure at the 5' end of the reporter probe, such as a stem-loop (or hairpin) as described in, for instance, U.S. Pat. No. 5,928,869, or a G-quartet as described in, for example, U.S. Pat. No. 5,691,145. The secondary structure may be labeled such that the donor and quencher are in close proximity when the secondary structure is folded, resulting in quenching of donor fluorescence. In the presence of target, the secondary structure may then be unfolded in a target-dependent primer extension reaction so that the distance between the donor and quencher is increased. This decreases quenching and produces an increase in donor fluorescence that can be detected as an indication of the presence of the target sequence.

Alternatively, the reporter moiety may be a single-stranded sequence at the 5' end of the reporter probe which is labeled with the donor and quencher in sufficiently close proximity to produce quenching and which contains a single-stranded RERS as described in U.S. Pat. No. 5,846,726 and U.S. Pat. No. 5,919,630. In the single-stranded reporter probe, the RERS is not cleavable. However, in the presence of target, the single-stranded RERS is converted to double-stranded form in a target-dependent primer extension reaction and thereby becomes cleavable. Treatment with the appropriate restriction endonuclease cleaves the RERS between the two dyes, separating them into separate nucleic acid fragments. The associated increase in distance between the dyes results in reduced quenching of donor fluorescence which can be detected as an indication of the presence of the target sequence. In a further embodiment, an RERS reporter moiety may be rendered nickable in the target-dependent primer extension reaction, as taught in U.S. Pat. Nos. 5,846,726 and 5,919,630. In this embodiment, when the RERS is rendered double-stranded the restriction endonuclease nicks the strand to which the donor and quencher are linked. Polymerase extends from the nick, displacing from the reporter probe a single-stranded fragment linked to one of the dyes. This also increases the distance between the donor and quencher and results in an increase in donor fluorescence due to decreased quenching.

In some embodiments, such as PCR using detection by the real-time hybridization of a reporter probe (e.g. TAQMAN® detection, F. Hoffman-La Roche, Ltd. through exclusive licensee Applied Biosystems, Foster City, Calif.), the reporter probe may contain a sequence that is identical to a sequence present in either strand of the amplicon. In such embodiments, the reporter probe may have a sequence specific to the target sequence, or may have a sequence common to a class of amplified nucleic acids, such as a sequence common to the genomes of influenza viruses. In the latter embodiments, specificity of the detection to a particular strain or the like can be obtained by the use of specific primer sequences. The label of the reporter probe is detected as an indication of the presence of a complement of the reporter probe, thereby indicating the presence of or the amplification of the target.

In SDA embodiments of the invention, the 3' terminus of the reporter probe may be capped to prevent extension by polymerase or it may be made extendible through the incorporation of a 3' terminal hydroxyl group. Capping may enhance performance in SDA embodiments by reducing background signal and the nonproductive consumption of reagents in spurious side-reactions resulting from the formation of primer dimers and other errant priming events. Examples of caps that prevent 3' extension of the reporter probe by polymerase enzymes include: substitution of the 3'-hydroxyl with a phosphate group, 3'-biotinylation or incorporation of a non-extendable inverted nucleotide base (3'-5' linkage) at the 3' end of the probe.

Any nucleic acid sequence or structure that may be labeled such that the presence of its complement, generated according to the methods of the invention, indicates the presence of the target sequence, may serve as a basis for a reporter probe.

In a further embodiment, a RERS reporter moiety may be rendered nickable in the target-dependent primer extension reaction, as taught in, for example, U.S. Pat. Nos. 5,846,726 and 5,919,630. In this embodiment, when the RERS is rendered double-stranded the restriction endonuclease nicks the strand to which the donor and quencher are linked. A polymerase extends from the nick, displacing from the reporter probe a single-stranded fragment linked to the fluorophore or to the quencher. This also increases the distance between the donor and quencher and results in an increase in a fluorescence signal due to decreased quenching.

In embodiments using direct detection of the amplicon, the reporter moiety may be a directly emitting moiety, such as, for instance, a fluorescent or chemiluminescent molecule. The reporter moiety could alternatively be a short nucleotide sequence that is distinct from the target sequence, or may be a molecule that is one member of a complex, such that the reporter is detected or quantified by measuring complex formation. Examples of such embodiments include hapten-antibody complexes and peptide-aptamer complexes.

Primers of the present invention typically are preferably designed with a minimum melting temperature ($T_m$) for the annealing region of 44° C., for use at an optimum temperature for SDA of 52.5° C. under the reaction conditions described in Examples 4 and 5.

EXAMPLES

The present invention is exemplified by the following examples. The examples set forth herein are illustrative only and are not intended to in any way limit the scope of the present invention.

Example 1

Primer Design

The primers and probes of the present invention, exemplified by those listed in Table 1, are designed by alignment of published matrix gene sequences using Lasergene MegAlign™ Software V5.06 (DNAStar®, Madison Wis.). Three thousand and thirty one influenza A, and seventy one influenza B matrix gene sequences were aligned by the ClustalW method to identify conserved regions of homology within each species. (See, Higgins et al., *CABIOS,* 5(2):151-153, 1989). For influenza A, separate alignments are performed for each of three source species: human (1392 sequences covering 7 subtypes), swine (162 sequences covering 9 subtypes) and avian (1477 sequences covering 95 subtypes); for influenza B a single alignment event was performed (71 sequences). These strains were selected for inclusion in the influenza A and B alignments to maximize amplification efficiency for all relevant influenza strains in each of the influenza A and B RT-SDA designs.

Primer and probe sequences for reverse transcriptase-SDA (RT-SDA) are designed to enable detection of all strains of influenza A and B and to enable discrimination between influenza A and influenza B. The aligned sequences are screened for BsoBI restriction recognition sites that would preclude their use in SDA-based amplification systems that employ the BsoBI restriction enzyme. Because both (+) and (−) strand viral RNA may be present in a clinical specimen, complementary amplification primers are designed for both strands of RNA, to facilitate cDNA synthesis. In RT-SDA, hybridization and extension of the amplification primers by the reverse transcriptase enzyme leads to displacement into solution of the downstream extension products of the signal primers, thereby facilitating subsequent amplification. (See, Hellyer T J. & Gillespie S H (ed), "Antibiotic Resistance methods and Protocols," Humana, Totowa, N.J., pp. 141-155, 2000).

For both influenza A and influenza B, amplification primers are designed to amplify conserved regions of the matrix gene such that there are a minimal number of mismatches between the primers and the target sequence. For both influenza A and B, oligonucleotide primers are positioned such that any mismatches with the target sequence are located away from the 3' terminus of the hybridization region. Thus, these possible mismatches have minimal impact on primer extension efficiency. Additionally, the length of the SDA amplicons is minimized to provide optimum amplification efficiency. Primers are screened for potential dimer formation using OLIGO® V6.67 software (Molecular Biology Insights, Inc., Cascade Colo.). Primers exemplified as those listed as SEQ ID NOS: 3-14, 17 and 18 are designed with a minimum melting temperature ($T_m$) for the annealing region of 44° C., for use at an optimum temperature for SDA of 52.5° C. under the reaction conditions described in Examples 4 and 5.

Example 2

Cloning of an Influenza A Target Sequence

Nucleic acid is isolated from an influenza A viral stock obtained from the American Type Culture Collection (ATCC) (culture number VR-547), using a QIAamp® Viral RNA Minikit (QIAGEN®, Valencia, Calif., USA). Oligonucleotides FAM-BL and FAM-RB (SEQ ID NOS: 3 and 4, respectively) are used to amplify a 158 base pair fragment by reverse transcription PCR.

Amplified DNA is cloned into *Escherichia coli* using a pCR® II-TOPO® vector (INVITROGEN™, Carlsbad, Calif., USA). Cloned plasmid DNA is purified and linearized by digestion with EcoRV restriction enzyme. Following repurification using a QIAquick® spin column (QIAGEN®) to remove the restriction enzyme, the DNA is then used as a template for generation of in vitro transcripts using a MEGASCRIPT® SP6 Kit (AMBION®, Austin, Tex., USA). Briefly, RNA polymerase is used to generate multiple RNA copies of the DNA template beginning at the SP6 promoter site upstream of the cloned influenza target sequence and extending through to the 3' end of the linearized plasmid. The RNA transcripts are then quantified by ultraviolet spectrophotometry and diluted to working concentration in water containing 10 ng/μl yeast RNA as a carrier.

Example 3

Cloning of an Influenza B Target Sequence

Nucleic acid is isolated from an influenza B viral stock obtained from the ATCC (culture number B/HIC/5/72) using a QIAAMP® Viral RNA Minikit (QIAGEN®). Oligonucleotides FBM-LB and FBM-RB (SEQ ID NOS: 5 and 6, respectively) are then used to amplify a 187 base pair fragment by reverse transcription PCR.

Amplified DNA is inserted into the pCR II-TOPO vector. Plasmid DNA is purified and linearized by digestion with BamHI restriction enzyme. The DNA is then repurified using a QIAQUICK® spin column (QIAGEN®) and quantified by ultraviolet analysis.

In vitro transcripts are then generated from the BamHI digested influenza B plasmid using a MEGASCRIPT T7 Kit (AMBION®). The RNA are quantified by ultraviolet spectrophotometry and diluted to working concentration in water containing 10 ng/μl yeast RNA as a carrier.

Example 4

Amplification of Cloned Influenza A and Influenza B RNA

Influenza A

Following a pre-warming step of microtiter plate wells containing avian myeloblastosis virus-RT (AMV-RT), ribonuclease inhibitor protein and all the oligonucleotides required for RT-SDA of influenza A RNA, a two-step RT-SDA assay is performed in which 75 copies of in vitro transcript RNA are first copied to cDNA using AMV-RT and then amplified in a conventional SDA reaction. Reverse transcription is carried out in microtiter wells with 10 units of AMV-RT in buffer containing: 120 mM bicine, 25 mM KOH, 43.5 mM $KPO_4$, 5% glycerol, 5% DMSO, 150 ng/μl BSA, 6 ng/μl yeast RNA, 5 mM magnesium acetate, 300 nM each of the following nucleotides: dATP, dGTP, and dTTP, 1500 nM dCsTP, 300 nM amplification primer FAM-BL (SEQ ID NO:2), 300 nM amplification primer FAM-RB (SEQ ID NO:3), 1500 nM signal primer FAM-LP (SEQ ID NO:7), 300 nM signal primer FAM-RP (SEQ ID NO:8), 750 nM adapter primer FAM-AD (SEQ ID NO:11), 750 nM adapter primer FAMICA.2 (SEQ ID NO: 13), 900 nM target detector mpc.DR (SEQ ID NO:15) and 900 nM internal control detector mpc2.FD (SEQ ID NO:16).

In vitro cloned internal control transcript is incorporated into the influenza A reverse transcription reaction at 7.5 copies/μL. In vitro cloned internal control transcript is incorporated into the influenza B reverse transcription reaction at 2.0 copies/μL.

The influenza A internal control molecule is constructed by inverse-PCR site-directed mutagenesis of the clone of the influenza A target region described in Example 2. Design of outward-facing PCR primers incorporate a 7-base mutation at the 3' end of the influenza A signal primer hybridization region. Inverse PCR is performed with Pfu DNA polymerase (STRATAGENE®) and the ends of the product are ligated to generate a circular plasmid molecule. The circular plasmid molecule is then electroporated into *E. coli*. The transformed *E. coli* is then grown to confluence and the plasmid is isolated and purified. Linearizing the cloned plasmid using EcoR V restriction enzyme, and performing an in vitro transcription reaction using an Ambion MEGAscript™ SP6 Kit, according to the manufacturer's instructions, generates in vitro transcripts. The resulting internal amplification control transcripts amplify and can be detected with similar efficiency to native influenza A target RNA but the two can be distinguished when co-amplified in the same RT-SDA reaction using specific signal primers and reporter probes labeled with different dyes. For detection of the influenza A internal amplification control, signal primer FAMICA.2 (SEQ ID 13) and reporter probe mpc2.FD (SEQ ID 16) are included in the reaction mixture, as described above.

Reverse transcription reactions are incubated at 52° C. for 5 minutes, then 100 μl buffer is added to modify conditions to those suitable for SDA (143 mM bicine, 82 mM KOH, 24.5 mM $KPO_4$, 12.5% DMSO, 1.67% glycerol). Microtiter plate wells were immediately transferred to 72° C. for 10 minutes to denature the AMV-RT enzyme and eliminate non-specific hybridization of primers. The reaction (100 μl) is then transferred to wells, pre-warmed to 52° C., containing Bst polymerase and BsoBI restriction enzyme to bring the final conditions to 143 mM bicine, 82 mM KOH, 24.5 mM $KPO_4$, 12.5% DMSO, 1.67% glycerol, 100 ng/μl BSA, 2 ng/μl yeast RNA, 100 nM each of dATP, dGTP, dTTP, 500 nM dCsTP, 6.7 mM magnesium acetate, 100 nM amplification primer FAM-BL (SEQ ID NO:3), 100 nM amplification primer FAM-RB (SEQ ID NO:4), 500 nM signal primer FAM-LP (SEQ ID NO:7), 100 nM signal primer FAM-RP (SEQ ID NO:8), 250 nM adapter primer FAM-AD (SEQ ID NO:11), 250 nM adapter primer FAMICA.2 (SEQ ID NO: 13), 300 nM target reporter mpc.DR (SEQ ID NO:15), 300 nM internal control reporter mpc2.FD (SEQ ID NO:16), approximately 800 units Bst and approximately 265 units BsoBI.

Reactions are sealed and incubated at 52° C. for 60 minutes in a BD PROBETEC™ ET fluorescence reader (BECTON-DICKINSON®, Franklin Lakes, N.J., US). Fluorescence is monitored over 60 passes of the instrument and results are expressed in terms of PAT scores (defined as 60−(number of passes required for relative fluorescent signal to pass a predetermined threshold)). PAT values equal to zero are considered negative whereas PAT scores greater than zero are considered positive. Results are shown in Tables 2 and 4.

Influenza B

A two-step RT-SDA assay is performed, as described above for influenza A, in which RNA is first copied to cDNA using AMV-RT. The reaction is conducted essentially as disclosed above for influenza A, with the exception that bumper primers FBM-LB (SEQ ID NO: 5) and FBM-RB (SEQ ID NO:6), amplification primers FBM-LP (SEQ ID NO:10) and FBM-RP (SEQ ID NO:11) and signal primers FBM-AD (SEQ ID NO:12) and FBMICA.2 (SEQ ID NO:14) are substituted for the corresponding influenza A-specific primers.

The approach to design and cloning of the influenza B internal control is similar to that adopted for the influenza A RT-SDA assay. The influenza B internal amplification control molecule is constructed by inverse PCR mutagenesis of a 6-base sequence that corresponds to the 3' end of the influenza B specific signal primer hybridization region. In vitro transcripts are generated using an AMBION MEGASCRIPT® T7 Kit as described by the manufacturer. For detection of the influenza B internal amplification control, signal primer FBMICA.2 (SEQ ID 14) and reporter probe mpc2.FD (SEQ ID 16) are included in the reaction mixture. Results are shown in Tables 3 and 5.

Example 5

Specificity of the Influenza A and B RT-SDA Assay

RNA is extracted from cultured stocks of influenza A and B using a QIAGEN® QIAAMP® viral RNA minikit procedure modified to include an on-column DNase treatment using 27.3 Kunitz units of RNase-free DNase I (QIAGEN®, Valencia, Calif., US) following the initial wash step with buffer AW1. A 15 minute DNase incubation at ambient temperature is performed after an initial Buffer AW1 wash step. Following the DNase incubation, a second Buffer AW1 wash step is performed and the standard QIAAMP® Viral RNA Mini Kit procedure is followed, with the exception that the purified nucleic acid is eluted in 80 μL Buffer AVE.

Nucleic acid is similarly isolated from stocks of other viruses and bacteria that commonly cause respiratory infections except that for bacterial species, no DNase treatment (and, thus, no second Buffer AW1 wash step) is performed. Purified nucleic acid is tested in each of the RT-SDA influenza A and influenza B assays in a similar manner to that described in Example 4, with the exception that no pre-incubation of microwells is performed prior to reverse transcription.

Influenza A and B purified RNAs are tested in their respective assays: at approximately 500 genome equivalents per test for Influenza A and 250 genome equivalents per test for Influenza B. All other purified nucleic acid stocks are tested at approximately $10^6$ genome equivalents per reaction. The influenza A and B assays are performed in similar manner to that described in Example 4.

General Conclusions

All stocks of influenza A tested in the influenza A assay yielded positive results at 500 particles per test with no false positive signals from the non-influenza A organisms, including influenza B. (See, Tables 2-9). Similarly, all stocks of influenza B tested in the influenza B assay gave positive results at 250 particles per test with no false positive results generated by non-influenza B organisms, including influenza A. (See, Tables 2-9).

Example 6

Specific Amplification of Cloned Influenza A and Influenza B RNA by RT-PCR

Influenza A: RT-PCR is performed wherein 10, 100, 500 and 1000 copies of in vitro transcript RNA are copied to form the related cDNA and amplified, using Brilliant™ QRT-PCR Master Mix (Stratagene), in a single-step, homogeneous reaction. RNA transcripts containing the targeted sequence within the matrix gene of the influenza A genome are prepared from a plasmid DNA clone as described in Example 2. Dilutions of target transcript RNA are prepared in nuclease-free water (Ambion, Inc.). PCR primers and TAQMAN™ probe (SEQ ID NOS:27-77), reverse transcriptase mix, and PCR master mix are combined with target RNA transcript in a single PCR tube in a total reaction volume of 50 μL. The final concentrations of primer FluATMLP1 (for instance, any one of SEQ ID NOS:27-30), primer FluATMRP2 (for instance, any one of SEQ ID NOS:65-68) and TAQMAN™ probe FluATMProbe3 (for instance, any one of SEQ ID NOS:47-62) are 200 nM, 200 nM and 100 nM, respectively. Reaction mixtures without reverse transcriptase enzyme are included to control for the presence of contaminating DNA from the parental plasmid clone of the target transcripts. RT-PCR is carried out in a Stratagene Mx3005P real-time PCR instrument. Reverse transcription is performed at 48° C. for 30 minutes, after which PCR amplification is conducted under the following cycling parameters: 95° C. for 10 minutes, then 40 cycles of 95° C. for 15 seconds and 59° C. for 1 minute.

Results are expressed in terms of cycle threshold (Ct); the point at which the background-corrected fluorescent signal crossed a predetermined threshold. The algorithm used to compute Ct values first identifies the portion of the amplification plots where all of the data curves within a run display an exponential increase in fluorescence, then calculates the threshold value that minimizes the standard deviation for Ct values within a given set of replicates. All (100%) reactions containing ≥100 RNA transcripts yielded positive results, with a mean Ct value of 34.3. None of the replicates of the "No Reverse Transcriptase" control generated positive results.

These data empirically demonstrate the ability to detect the targeted sequence of the influenza A matrix gene using the disclosed primers and detector probe.

Influenza B: RT-PCR is performed in which 10, 100, 500 and 1000 copies of in vitro transcript RNA were copied into cDNA and amplified, using BRILLIANT™ QRT-PCR Master Mix (Stratagene), in a single-step, homogeneous reaction. RNA transcripts containing the targeted sequence within the matrix gene of the influenza B genome are prepared from a plasmid DNA as described in Example 2. Dilutions of target transcript RNA are prepared in nuclease-free water (Ambion, Inc.). PCR primers, TAQMAN™ probe, reverse transcriptase mix, and PCR master mix are combined with target RNA transcript in a single PCR tube in a total reaction volume of 50 μL. The final concentrations of primer FluBTMLP1 (SEQ ID NO:69), primer FluBTMRP1 (for instance, any one of SEQ ID NOS:74-77) and TAQMAN™ probe FluBTMProbe3 (for instance, any one or more of SEQ ID NOS:70-73) are 200 nM, 200 nM and 100 nM, respectively. Reaction mixtures without reverse transcriptase enzyme are included to control for the presence of contaminating DNA from the parental plasmid clone of the target transcripts. RT-PCR is carried out in a Stratagene Mx3005P real-time PCR instrument. Reverse transcription is performed at 48° C. for 30 minutes, after which PCR amplification is conducted under the following cycling parameters: 95° C. for 10 minutes, then 40 cycles of 95° C. for 15 seconds and 59° C. for 1 minute.

Results are expressed in cycle threshold (Ct), the point at which the background-corrected fluorescent signal crossed a predetermined threshold. The algorithm used to compute Ct values first identifies the portion of the amplification plots where all of the data curves within a run display an exponential increase in fluorescence, then calculates the threshold value that minimizes the standard deviation for Ct values within a given set of replicates. All (100%) reactions containing≥100 RNA transcripts yielded positive results, with a mean Ct value of 31.4. Two of four replicates of the "No Reverse Transcriptase" control crossed the positive threshold with Ct scores>37, indicating the presence of low levels of DNA contamination. Assuming an amplification efficiency of 2, these results indicate approximately a 64-fold difference in input target level between these samples and those containing 100 copies of transcript RNA.

These data demonstrate the ability to detect the targeted sequence of the influenza B matrix gene using the disclosed primers and detector probe.

All references, including publications, patents, and patent applications, cited herein are hereby incorporated by reference to the same extent as if the disclosure each reference were individually and specifically indicated to be incorporated by reference and were set forth in its entirety herein.

TABLE 2

| Influenza A Assay | | | |
|---|---|---|---|
| | PAT Score | | |
| Target | Target | Internal Control | Result |
| No target spike | 0.0 | 43.3 | Negative |
| No target spike | 0.0 | 44.1 | Negative |
| No target spike | 0.0 | 47.5 | Negative |
| No target spike | 0.0 | 48.0 | Negative |
| No target spike | 0.0 | 47.0 | Negative |
| No target spike | 0.0 | 46.1 | Negative |
| No target spike | 0.0 | 48.0 | Negative |
| No target spike | 0.0 | 46.1 | Negative |
| 750 copies/reaction | 48.2 | 44.1 | Positive |
| 750 copies/reaction | 44.7 | 15.4 | Positive |
| 750 copies/reaction | 45.0 | 28.9 | Positive |
| 750 copies/reaction | 40.7 | 39.7 | Positive |
| 750 copies/reaction | 48.8 | 43.1 | Positive |
| 750 copies/reaction | 49.4 | 48.7 | Positive |
| 750 copies/reaction | 49.1 | 47.2 | Positive |
| 750 copies/reaction | 49.8 | 38.1 | Positive |

TABLE 3

| Influenza B Assay | | | |
|---|---|---|---|
| | PAT Score | | |
| Target | Target | Internal Control | Result |
| No target spike | 0.0 | 49.1 | Negative |
| No target spike | 0.0 | 49.2 | Negative |
| No target spike | 0.0 | 49.1 | Negative |
| No target spike | 0.0 | 48.6 | Negative |
| No target spike | 0.0 | 42.5 | Negative |
| No target spike | 0.0 | 49.2 | Negative |
| No target spike | 0.0 | 49.3 | Negative |
| No target spike | 0.0 | 49.9 | Negative |
| 200 copies/reaction | 42.9 | 46.8 | Positive |

TABLE 3-continued

| Influenza B Assay | | | |
|---|---|---|---|
| | PAT Score | | |
| Target | Target | Internal Control | Result |
| 200 copies/reaction | 41.5 | 48.2 | Positive |
| 200 copies/reaction | 47.5 | 45.7 | Positive |
| 200 copies/reaction | 47.8 | 47.4 | Positive |
| 200 copies/reaction | 44.1 | 48.6 | Positive |
| 200 copies/reaction | 42.1 | 48.3 | Positive |
| 200 copies/reaction | 45.6 | 48.1 | Positive |
| 200 copies/reaction | 46.6 | 47.4 | Positive |

TABLE 4

Influenza A Viral Stocks Tested in the Influenza A RT-SDA Assay

| Virus | ID | test level | Mean PAT Score | # Replicates Positive |
|---|---|---|---|---|
| Influenza A | ATCC VR219 | 500 genome equivalents/test | 45.5 | 4 |
| Influenza A | ATCC VR897 | 500 genome equivalents/test | 42.9 | 4 |
| Influenza A | ATCC VR544 | 500 genome equivalents/test | 43.9 | 4 |
| Influenza A | ATCC VR547 | 500 genome equivalents/test | 44.4 | 4 |
| Influenza A | ATCC VR825 | 500 genome equivalents/test | 45.6 | 4 |
| Influenza A | ATCC VR1520 | 500 genome equivalents/test | 39.8 | 4 |

TABLE 5

Influenza B Viral Stocks Tested in the Influenza A RT-SDA Assay

| Virus | ID | test level | Mean PAT Score | # Replicates Positive |
|---|---|---|---|---|
| Influenza B | ATCC VR101 | $10^6$ genome equivalents/test | 0 | 4 |
| Influenza B | ATCC VR790 | $10^6$ genome equivalents/test | 0 | 4 |
| Influenza B | CDC 98010029 | $10^6$ genome equivalents/test | 0 | 4 |

TABLE 7

Influenza B Viral Stocks Tested in the Influenza B RT-SDA Assay

| Virus | ID | test level | Mean PAT Score | # Replicates Positive |
|---|---|---|---|---|
| Influenza B | ATCC VR101 | 250 genome equivalents/test | 48.1 | 4 |
| Influenza B | ATCC VR790 | 250 genome equivalents/test | 43.8 | 4 |
| Influenza B | CDC 98010029 | 250 genome equivalents/test | 49.6 | 4 |

TABLE 8

Influenza A Viral Stocks Tested in the Influenza B RT-SDA Assay

| Virus | ID | test level | Mean PAT Score | # Replicates Negative |
|---|---|---|---|---|
| Influenza A | ATCC VR219 | $10^6$ genome equivalents/test | 0.0 | 4 |
| Influenza A | ATCC VR897 | $10^6$ genome equivalents/test | 0.0 | 4 |
| Influenza A | ATCC VR544 | $10^6$ genome equivalents/test | 0.0 | 4 |
| Influenza A | ATCC VR547 | $10^6$ genome equivalents/test | 0.0 | 4 |
| Influenza A | ATCC VR825 | $10^6$ genome equivalents/test | 0.0 | 4 |
| Influenza A | ATCC VR1520 | $10^6$ genome equivalents/test | 0.0 | 4 |

TABLE 6

Non-Influenza Bacterial and Viral Stocks Tested in the Influenza A RT-SDA Assay

| Organism | ID | test level | Mean PAT Score | Replicates Negative |
|---|---|---|---|---|
| *Staphylococcus aureus* | 12598 | $10^6$ genome equivalents/reaction | 0 | 2 |
| *Streptococcus pneumoniae* | ATCC 6303 | $9.22 \times 10^5$ genome equivalents/reaction | 0 | 2 |
| *Chlamydia psittaci* | VR-601 | $10^6$ genome equivalents/reaction | 0 | 2 |
| *Legionella pneumophila* | ATCC 33152 | $10^6$ genome equivalents/reaction | 0 | 2 |
| *Legionella micdadei* | ATCC 33204 | $10^6$ genome equivalents/reaction | 0 | 2 |
| *Bordatella bronchiseptica* | ATCC 10580 | $10^6$ genome equivalents/reaction | 0 | 2 |
| *Chlamydophila pneumoniae* | TW-183 | $10^6$ genome equivalents/reaction | 0 | 2 |
| *Haemophilus influenza* | ATCC 33533 | $10^6$ genome equivalents/reaction | 0 | 2 |
| *Bordatella pertussis* | 53984 | $10^6$ genome equivalents/reaction | 0 | 2 |
| *Mycoplasma pneumoniae* | 29342 | $10^6$ genome equivalents/reaction | 0 | 2 |
| *Rhinovirus* | 1A | $10^6$ genome equivalents/reaction | 0 | 2 |
| *Rhinovirus* | 70 | $10^6$ genome equivalents/reaction | 0 | 2 |

TABLE 9

Non-Influenza Bacterial and Viral Stocks Tested in the Influenza B RT-SDA Assay

| Organism | ID | test level | Mean PAT Score | Replicates Negative |
|---|---|---|---|---|
| *Staphylococcus aureus* | 12598 | $10^6$ genome equivalents/reaction | 0 | 2 |
| *Streptococcus pneumoniae* | ATCC 6303 | $9.22 \times 10^5$ genome equivalents/reaction | 0 | 2 |
| *Chlamydia psittaci* | VR-601 | $10^6$ genome equivalents/reaction | 0 | 2 |
| *Legionella pneumophila* | ATCC 33152 | $10^6$ genome equivalents/reaction | 0 | 2 |
| *Legionella micdadei* | ATCC 33204 | $10^6$ genome equivalents/reaction | 0 | 2 |
| *Bordatella bronchiseptica* | ATCC 10580 | $10^6$ genome equivalents/reaction | 0 | 2 |
| *Chlamydophila pneumoniae* | TW-183 | $10^6$ genome equivalents/reaction | 0 | 2 |
| *Haemophilus influenza* | ATCC 33533 | $10^6$ genome equivalents/reaction | 0 | 2 |
| *Bordatella pertussis* | 53984 | $10^6$ genome equivalents/reaction | 0 | 2 |
| *Mycoplasma pneumoniae* | 29342 | $10^6$ genome equivalents/reaction | 0 | 2 |
| *Rhinovirus* | 1A | $10^6$ genome equivalents/reaction | 0 | 2 |
| *Rhinovirus* | 70 | $10^6$ genome equivalents/reaction | 0 | 2 |

What is claimed is:

1. A method for detecting the presence of influenza B in a sample, said method comprising:

a) amplifying an influenza B matrix gene target nucleic acid, if present in the sample, using at least two oligonucleotide primers, wherein said two oligonucleotide primers are:

i) SEQ ID NO: 69; and ii) SEQ ID NO: 76 to produce an amplified influenza B matrix gene target nucleic acid product; and b) detecting the amplified influenza B matrix gene target nucleic acid product, wherein detection of the amplified influenza B matrix gene target nucleic acid product indicates the presence of influenza B in the sample.

2. The method of claim 1, wherein detecting the amplified influenza B matrix gene target nucleic acid product is conducted by hybridization to an oligonucleotide probe.

3. The method of claim 2, wherein the oligonucleotide probe is one of SEQ ID NOS: 70-73.

4. The method of claim 2, wherein the influenza B matrix gene target nucleic acid is amplified by Polymerase Chain Reaction.

5. The method of claim 3, wherein the oligonucleotide probe is a reporter probe further comprising a detectable moiety, wherein the detectable moiety is selected from the group consisting of: fluorescein isothiocyanate (FITC)/N-tetramethylrhodamine isothiocyanate (TRITC), FITC/Sulforhodamine 101 acid chloride, FITC/N-hydroxysuccinimidyl 1-pyrenebutyrate (PYB), FITC/eosin isothiocyanate (EITC), FITC/rhodamine X, FITC/tetramethylrhodamine, P-(dimethyl aminophenylazo) benzoic acid (DABCYL), 5-(2'-aminoethyl) aminonapthalene, rhodamine, fluorescein, 32P, 35S, horseradish peroxidase, alkaline phosphatase, glucose oxidase, galactosidase, soybean peroxidase, luciferase, digoxigenin, biotin and 2,4-dinitrophenyl.

6. The method of claim 5, wherein the oligonucleotide probe further comprises a restriction enzyme cleavage site, herein said restriction enzyme cleavage site is selected from the group of sites consisting of: BsoBi, HincII, AvaI, NciI and Fnu4HI.

7. The method of claim 1, wherein the influenza B matrix gene target nucleic acid comprises SEQ ID NO: 26.

8. A method for detecting the presence of influenza B in a sample, said method comprising:

a) amplifying an influenza B matrix gene target nucleic acid, if present in the sample, using at least two oligonucleotide primers, wherein said two oligonucleotide primers are:

i) SEQ ID NO 69; and ii) any one of SEQ ID NOS: 74-76 to produce an amplified influenza B matrix gene target nucleic acid product; and b) detecting the amplified influenza B matrix gene target nucleic acid product by hybridization to an oligonucleotide probe, wherein the oligonucleotide probe is one of SEQ ID NOS: 72-73, wherein detection of the amplified influenza B matrix gene target nucleic acid product indicates the presence of influenza B in the sample.

9. The method of claim 8, wherein the influenza B matrix gene target nucleic acid is amplified by Polymerase Chain Reaction.

10. The method of claim 8, wherein the oligonucleotide probe is a reporter probe further comprising a detectable moiety, wherein the detectable moiety is selected from the group consisting of: fluorescein isothiocynate (FITC)/tetramethylrhodamine isothiocyanate (TRITC), FITC/Sulforhodamine 101 acid chloride, FITC/N-hydroxysuccinimidyl 1-pyrenebutyrate (PYB), FITC/eosin isothiocyanate (EITC), FITC/rhodamine X, FITC/tetramethylrhodamine, P-(dimethyl aminophenylazo) benzoic acid (DABCYL), 5-(2'-aminoethyl) aminonapthalene, rhodamine, fluorescein, 32P, 35S, horseradish peroxidase, alkaline phosphatase, glucose oxidase, galactosidase, soybean peroxidase, luciferase, digoxigenin, biotin and 2,4-dinitrophenyl.

11. The method of claim 10, wherein the oligonucleotide probe further comprises a restriction enzyme cleavage site, wherein said restriction enzyme cleavage site is selected from the group of sites consisting of: BsoBi, HincII, AvaI, NciI and Fnu4HI.

12. The method of claim 8, wherein the influenza B matrix gene target nucleic acid comprises SEQ ID NO: 26.

13. A method for detecting the presence of influenza B in a sample, said method comprising:

a) amplifying an influenza B matrix gene target nucleic acid, if present in the sample, using at least two oligonucleotide primers, wherein said two oligonucleotide primers are:

i) SEQ ID NO: 69; and ii) any one of SEQ ID NOS: 74-76 to produce an amplified influenza B matrix gene target nucleic acid product; and b) detecting the amplified influenza B matrix gene target nucleic acid product by hybridization to an oligonucleotide probe, wherein the oligonucleotide probe comprises one of SEQ ID NOS: 72-73 with one or more substitutions selected from the group consisting of:

position 20 of SEQ ID NOS: 72-73 substituted with inosine or xanthine, and position 21 of SEQ ID NOS: 72-73 substituted with inosine;

wherein detection of the amplified influenza B matrix gene target nucleic acid product indicates the presence of influenza B in the sample.

14. A method for amplifying influenza B in a sample, said method comprising:

a) amplifying an influenza B matrix gene target nucleic acid, if present in the sample, using at least two oligonucleotide primers, wherein said two oligonucleotide primers are:

i) SEQ ID NO: 69; and ii) SEQ ID NO: 76 with one or more substitutions selected from the group consisting of:

position 1 of SEQ ID NO: 76 substituted with inosine, and position 13 of SEQ ID NO: 76 substituted with inosine or xanthine.

* * * * *